US007910368B2

(12) United States Patent
Sagawa et al.

(10) Patent No.: US 7,910,368 B2
(45) Date of Patent: Mar. 22, 2011

(54) METHOD OF EXTENDED CULTURE FOR ANTIGEN-SPECIFIC CYTOTOXIC LYMPHOCYTES

(75) Inventors: Hiroaki Sagawa, Kusatsu (JP); Mitsuko Ideno, Kyoto (JP); Ikunoshin Kato, Shiga (JP)

(73) Assignee: Takara Bio Inc., Otsu-shi (JP)

( * ) Notice: Subject to any disclaimer, the term of this patent is extended or adjusted under 35 U.S.C. 154(b) by 86 days.

(21) Appl. No.: 10/486,512

(22) PCT Filed: Aug. 15, 2002

(86) PCT No.: PCT/JP02/08298
§ 371 (c)(1),
(2), (4) Date: Feb. 12, 2004

(87) PCT Pub. No.: WO03/016511
PCT Pub. Date: Feb. 27, 2003

(65) Prior Publication Data
US 2005/0042208 A1 Feb. 24, 2005

(30) Foreign Application Priority Data

Aug. 15, 2001 (JP) ................. 2001-246747
Dec. 11, 2001 (JP) ................. 2001-376966
Mar. 25, 2002 (JP) ................. 2002-084428

(51) Int. Cl.
C12N 5/08 (2006.01)
C12N 5/00 (2006.01)
(52) U.S. Cl. .................. 435/372.3; 435/373; 435/405
(58) Field of Classification Search ............... None
See application file for complete search history.

(56) References Cited

U.S. PATENT DOCUMENTS

| 5,102,988 | A | 4/1992 | Kimizuka et al. |
| 5,198,423 | A | 3/1993 | Taguchi et al. |
| 5,354,686 | A | 10/1994 | Haberman |
| 5,827,642 | A * | 10/1998 | Riddell et al. ............ 435/2 |
| 5,866,115 | A | 2/1999 | Kanz et al. |
| 6,316,257 | B1 * | 11/2001 | Flyer et al. ............ 435/372.3 |
| 6,692,964 | B1 | 2/2004 | June et al. |
| 6,734,014 | B1 * | 5/2004 | Hwu et al. ............ 435/325 |
| 6,821,778 | B1 * | 11/2004 | Engleman et al. ......... 435/372.3 |
| 7,067,318 | B2 | 6/2006 | June et al. |
| 7,172,869 | B2 | 2/2007 | June et al. |
| 2005/0042208 | A1 | 2/2005 | Sagawa et al. |
| 2005/0227354 | A1 | 10/2005 | Sagawa et al. |
| 2006/0166924 | A1 | 7/2006 | Kato et al. |
| 2006/0246587 | A1 | 11/2006 | June et al. |
| 2008/0227204 | A1 | 9/2008 | Sagawa et al. |

FOREIGN PATENT DOCUMENTS

| EP | 0207751 | 1/1987 |
| EP | 0 523 948 A3 | 1/1993 |
| EP | 523948 A2 | 1/1993 |
| EP | 0795606 A1 | 9/1997 |
| EP | 0 870 839 A1 | 10/1998 |
| EP | 1496109 | 1/2005 |
| JP | 4-297494 A | 10/1992 |
| JP | 6-306096 A | 11/1994 |
| JP | 9-25299 A | 1/1997 |
| JP | 2729712 B2 | 3/1998 |
| JP | 11-505419 A | 5/1999 |
| JP | 3104178 B2 | 10/2000 |
| JP | 2001-314183 A | 11/2001 |
| WO | WO-8901942 A1 | 3/1989 |
| WO | WO-9013653 | 11/1990 |
| WO | WO-95/04078 A1 | 2/1995 |
| WO | WO-95/11963 A1 | 5/1995 |
| WO | WO 95/28479 A1 | 10/1995 |
| WO | WO-96/00782 A1 | 1/1996 |
| WO | WO 96/6929 A2 | 3/1996 |
| WO | WO 96/06929 A2 | 3/1996 |
| WO | WO 96/16674 A1 | 6/1996 |
| WO | WO 97/05239 A1 | 2/1997 |
| WO | WO 97/5239 A1 | 2/1997 |
| WO | WO 97/11604 | * 3/1997 |
| WO | WO 97/18318 A1 | 5/1997 |
| WO | WO 97/32970 A1 | 9/1997 |
| WO | WO 97/329704 A1 | 9/1997 |
| WO | WO-9812306 | 3/1998 |
| WO | WO-9833888 | 8/1998 |
| WO | WO 99/33869 A2 | 7/1999 |

(Continued)

OTHER PUBLICATIONS

Galandrini et al., J. of Immunology, 1994,v.153, pp. 21-31.*
Johannes et al J. Clin. Invest, 1998,V.102, pp. 1051-1061.*
Davis et al., ( J of Immunology, 1990, vol. 145, pp. 785-793.*
Blue M., et al ., Cellular Immunol. 1991, v.138, 238-244.*
Masashi Tani et al., "Gan Tokuiteki Men'eki Ryoho-CTL Ryoho no Genjo to Shorai", Cancer Therapy & Host, 2000, vol. 12, No. 4, p. 330-5, p. 330, lower right part, col. 2.
Galandrini R. et al., Hyaluronate is costimulatory for human T cell effector functions and binds to CD44 on activated T cells., J. Immunol 1994, vol. 153, No. 1, pp. 21 to 31.
Seth A. et al., T-cell-receptor-independent activation of cytolytic activity of cytotoxic T lymphocytes mediated through CD44 and gp90$^{MEL-14}$., Proc. Natl. Acad. Sci. USA, 1991, vol. 88, No. 17, p. 7877-81.

(Continued)

Primary Examiner — Michail A Belyavskyi
(74) Attorney, Agent, or Firm — Birch, Stewart, Kolasch & Birch, LLP

(57) ABSTRACT

The present invention is a method for inducing cytotoxic T cell having an antigen-specific cytotoxic activity, a method for maintaining the cell, a method for continuously culturing the cell or a method for expanding the cell, comprising the step of culturing a cytotoxic T cell in the presence of at least one substance selected from the group consisting of (A) a substance having a binding activity to CD44; (B) a substance capable of regulating a signal emitted by binding a CD44 ligand to CD44; (C) a substance capable of inhibiting binding of a growth factor to a growth factor receptor; (D) a substance capable of regulating a signal emitted by binding of a growth factor to a growth factor receptor; and (E) fibronectin, a fragment thereof or a mixture thereof.

9 Claims, 6 Drawing Sheets

FOREIGN PATENT DOCUMENTS

| WO | WO-00/56368 A1 | 9/2000 |
| WO | WO-03/016511 A1 | 2/2003 |
| WO | WO-03/080817 A1 | 10/2003 |

OTHER PUBLICATIONS

Galandrini R. et al., Antibodies to CD44 trigger effector functions of human T cell clones., J. Immunol, 1993, vol. 150, No. 10, p. 4225-35.
Takahashi K. et al., Antigen-independent T cell activation mediated by a very late activation antigen-like extracellular matrix receptor., Eur J. Immunol, 1991, vol. 21, No. 6, p. 1559-62.
Atsushi Ariga et al., "Jujo Saibo o Mochiita CTL no Koshuyo Koka Zokyo", Biotherapy, 1998, vol. 12, No. 5, p. 875-7, p. 876, col. II.
Masashi Tani et al.; Cancer Therapy & Host, 2000, vol. 12, No. 4, pp. 330-335, lower right part, col. 2.
Ricciarda Galadrini et al.; J. Immunol. 1994, vol. 153, No. 1, pp. 21-31.
Aruna Seth et al.; Proc. Natl. Acad. Sci., vol. 88, pp. 7877-7811, Sep. 1991.
Ricciarda Galandrini et al.; The Journal of Immunology; vol. 150, pp. 4225-4235, No. 10, May 15, 1993.
Stanley R. Riddell et al.; Science, vol. 257, Jul. 10, 1992, pp. 238-241.
Stanley R. Riddell et al.; The Journal of Immunology; vol. 146, pp. 2795-2804, No. 8, Apr. 15, 1991.
Stanley R. Riddell et al.; Journal of Immunological Methods, vol. 128, 1990, pp. 189-201.
Erkki Ruoslahti et al.; The Journal of Biological Chemistry; vol. 256, No. 14, Issue of Jul. 25, 1989, pp. 7277-7281.
Kazuhisa Takahashi et al.; Eur. J. Immunol.; 1991, vol. 21, pp. 1559-1562.
Atsushi Aruga et al.; Biotherapy, 1998, vol. 12, No. 5, pp. 875-877.
Fusao Kimizuka et al.; J. Biochem. vol. 110, pp. 284-291, 1991.
Albert R. Kornblihtt et al.; The EMBO Journal; vol. 4, No. 7, pp. 1755-1759, 1985.
Kiyotoshi Sekiguchi et al.; Biochemistry, vol. 25, pp. 4936-4941, 1986.
Maria A. Bednarek et al.; The Journal of Immunology, vol. 147, No. 12, pp. 4047-4053, Dec. 15, 1991.
J. Carter et al.; Immunology; vol. 57, pp. 123-129, 1986.
Joseph P. Uberti et al.; Clinical Immunology and Immunopathology; vol. 70, No. 3, Mar. 1994, pp. 234-240.
Davis et al., The Journal of Immunology, vol. 145, No. 3, pp. 785-793, (Aug. 1990). XP-002381603.
Mizobata et al., British Journal of Cancer, vol. 74, pp. 1598-1604 (Nov. 1996). XP-008058177.
Ybarrondo et al., Immunology, vol. 91 No. 2, pp. 186-192, (Jun. 1997). XP-002362285.
Shimizu et al., The Journal of Immunology, vol. 145, No. 1, pp. 59-67 (Jul. 1, 1990). XP-002362286.
Avdalovic et al., Immunology Letters, vol. 35, No. 2, pp. 101-108, (Feb. 1993). XP-002381602.
Galandrini et al., "CD44 Triggering Enhances Human NK Cell Cytotoxic Functions," J. Immunol., vol. 153, pp. 4399-4407 (Nov. 1994) (Abstract Only).
Galandrini et al., "Ligation of the Lymphocyte Homing Receptor CD44 Triggers T-Helper and Cytolytic Functions of Human T-Cells," Cytotechnology, vol. 11, Suppl. 1, pp. 100-102 (1993) (Abstract Only).
Paul et al., "Long-term growth and cloning of non-transformed lymphocytes," Nature, vol. 294, pp. 697-699.
Lehnert et al., Eur. J. Immunol., 1998, vol. 28, pp. 3605-3615.
Shizuma Mizobata, J. Wakayama Med. Soc., 1995, vol. 46, No. 4, pp. 457-467.
Pozo et al., The Journal of Cell Biology, 1995, vol. 131, No. 2, pp. 495-508.
"Animal Cell Culture. Methods," edited by R. Freshney, Moscow, "Mir," 1989, pp. 26-41, the original English "Animal cell culture—a practical approach," edited by R. R. Freshney, IRL Press. Oxford. Washington D.C.
Gabriella Palmieri et al.; Journal of Immunology; vol. 155, No. 11, pp. 5314-5322, Dec. 1, 1995.
Michael D. Pierschbacher et al.; Cell; vol. 26, No. 2, pp. 259-267, Oct. 1981.
Nunclon product information, VWRLabshop, p. 1 (Website search date Apr. 19, 2007).
Ostergaard et al., Eur. J. lmmunol. vol. 25 (1995): 252-256.
Pollok et al., J. Virol. vol. 72 (1998): 4882-4892.
Chen et al., J. lmmunol. vol. 153 (1994): 3630-3638.
Yoneda et al., Exp. Cell Res. vol. 217 (1995): 169-179.
Rostagno et al., Biochem. J. vol. 338 (1999): 375-386.
Kornblihtt et al., FASEB J. vol. 10 (1996): 248-257.
Rao et al., J. lmmunol. vol. 165 (2000): 4935-4940.
Shuqin et al., "Journal of South China Normal University (Natural Science Edition)," No. 4, 1994, pp. 1-17.
Alberto R. Kornblihtt: Proc. Natl. Acad. Sci., USA, vol. 80, pp. 3218 to 3222 (1983).
Pina M. Cardarelli et al., Cell lmmunol. vol. 135, pp. 105 to 117 (1991).
Philip D. Greenberg; Advances in Immunology, vol. 49, pp. 281-355 (1991).
Pierre Reusser et al.; Blood, vol. 78, No. 5, pp. 1373-1380, Sep. 1, 1991.
Steven A. Rosenberg; The New England Journal of Medicine; vol. 316, No. 15, pp. 889-897; Apr. 9, 1987.
Steven a. Rosenberg: the New England Journal of Medicine; vol. 319, No. 25, pp. 1676-1680, Dec. 22, 1988.
Monto Ho et al.; Blood, vol. 81, No. 8, pp. 2093-2101, Apr. 15, 1993.
Torben E. Petersen et al.; Primary Structure of Fibronectin; Fibronectin; Edited by Deane F. Mosher, pp. 1-24, c. 1989.
Helmut Hanenberg et al., Human Gene Therapy, vol. 8, pp. 2193-2206, Dec. 10, 1997.
Shun et al., Zhongguo Haiyang Yaowu Drugs, 14(3): 9-13, 1995.
Kato et al. Jpn. J. Phycol.; Mar. 2000, vol. 48, pp. 13-19.
Kohei Noguchi et al., Anticancer Research, 1995, vol. 15, pp. 255-288.
Mizobata, J. Wakayama Med. Soc., 1995, 46, 457-467.
Genetic Medicine, 1999, 32:114-119.
USPTO Decision on Appeal, U.S. Appl. No. 10/344,534, May 28, 2010, pp. 1-12.
Paul et al., "Long-term growth and cloning of non-transformed lymphocytes," Nature, vol. 294, pp. 697-699, 1981.
E.W. Johnson, et al, "Expression and Function of Insulin-Like Growth Factor Receptors on Anti-CD3-Activated Human T Lymphyocytes", Journal of Immunology, Jan. 1, 1992, vol. 148, No. 1, pp. 63-71.
European Search Report, Application No. EP 09004189, Dec. 8, 2009, pp. 1-6.
S. Tamura, et al, "Expression and Function of c-Met, a Receptor for Hepatocyte Growth Factor, During T-Cell Development," Scandinavian Journal of Immunology, Apr. 1998, vol. 47, No. 4, pp. 296-301.
T. Kanto, et al, "Neutralization of Transforming Growth Factor Beta-1 Augments Hepatitis C Virus-Specific Cytotoxic T Lymphocyte Induction in Vitro", Journal of Clinical Immunology, Nov. 1997, vol. 17, No. 6, pp. 462-471.
Chinese Office Action for application No. 200480024172.7, dated Jan. 15, 2010.
Yu et al., "The Study of Human LAK and L1-LAK Cells' Proliferation and Activation of Antitumor in Vitro", Journal of Jinan University, Natural Science & Medicine Edition, Dec. 1998, pp. 56-60, vol. 19 Suppl.
Partial Search Report; mailed Aug. 6, 2009; pp. 1-3.
Funaro, et al.; Stimulation of T Cells via CD44 Requires Leukocyte-Function-Associated Antigen Interactions and Interleukin-2 Production; Human Immunology 40; Aug. 1994; pp. 267-278; vol. 40; No. 4.

* cited by examiner

SEQUENCE LISTING

```
<160> NUMBER OF SEQ ID NOS: 20

<210> SEQ ID NO 1
<211> LENGTH: 274
<212> TYPE: PRT
<213> ORGANISM: Artificial Sequence
<220> FEATURE:
<223> OTHER INFORMATION: Description of Artificial Sequence: Fibronectin
      fragment named C-274

<400> SEQUENCE: 1

Pro Thr Asp Leu Arg Phe Thr Asn Ile Gly Pro Asp Thr Met Arg Val
 1               5                  10                  15

Thr Trp Ala Pro Pro Pro Ser Ile Asp Leu Thr Asn Phe Leu Val Arg
            20                  25                  30
```

```
Tyr Ser Pro Val Lys Asn Glu Glu Asp Val Ala Glu Leu Ser Ile Ser
         35                  40                  45

Pro Ser Asp Asn Ala Val Val Leu Thr Asn Leu Leu Pro Gly Thr Glu
 50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
        130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
        210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp

<210> SEQ ID NO 2
<211> LENGTH: 25
<212> TYPE: PRT
<213> ORGANISM: Homo sapiens

<400> SEQUENCE: 2

Asp Glu Leu Pro Gln Leu Val Thr Leu Pro His Pro Asn Leu His Gly
 1               5                  10                  15

Pro Glu Ile Leu Asp Val Pro Ser Thr
             20                  25

<210> SEQ ID NO 3
<211> LENGTH: 271
<212> TYPE: PRT
<213> ORGANISM: Artificial Sequence
<220> FEATURE:
<223> OTHER INFORMATION: Description of Artificial Sequence: Fibronectin
      fragment named H-271

<400> SEQUENCE: 3

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
             20                  25                  30

Arg Val Arg Val Thr Pro Lys Glu Lys Thr Gly Pro Met Lys Glu Ile
```

```
                35                  40                  45
Asn Leu Ala Pro Asp Ser Ser Val Val Ser Gly Leu Met Val
 50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu Asn Val Ser Pro
                 85                  90                  95

Pro Arg Arg Ala Arg Val Thr Asp Ala Thr Glu Thr Thr Ile Thr Ile
                100                 105                 110

Ser Trp Arg Thr Lys Thr Glu Thr Ile Thr Gly Phe Gln Val Asp Ala
                115                 120                 125

Val Pro Ala Asn Gly Gln Thr Pro Ile Gln Arg Thr Ile Lys Pro Asp
130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
                180                 185                 190

Ala Thr Thr Pro Asn Ser Leu Leu Val Ser Trp Gln Pro Pro Arg Ala
                195                 200                 205

Arg Ile Thr Gly Tyr Ile Ile Lys Tyr Glu Lys Pro Gly Ser Pro Pro
                210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr
                260                 265                 270

<210> SEQ ID NO 4
<211> LENGTH: 296
<212> TYPE: PRT
<213> ORGANISM: Artificial Sequence
<220> FEATURE:
<223> OTHER INFORMATION: Description of Artificial Sequence: Fibronectin
      fragment named H-296

<400> SEQUENCE: 4

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
                 20                  25                  30

Arg Val Arg Val Thr Pro Lys Glu Lys Thr Gly Pro Met Lys Glu Ile
                 35                  40                  45

Asn Leu Ala Pro Asp Ser Ser Val Val Ser Gly Leu Met Val
 50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu Asn Val Ser Pro
                 85                  90                  95

Pro Arg Arg Ala Arg Val Thr Asp Ala Thr Glu Thr Thr Ile Thr Ile
                100                 105                 110

Ser Trp Arg Thr Lys Thr Glu Thr Ile Thr Gly Phe Gln Val Asp Ala
                115                 120                 125

Val Pro Ala Asn Gly Gln Thr Pro Ile Gln Arg Thr Ile Lys Pro Asp
```

```
                130                 135                 140
Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
                180                 185                 190

Ala Thr Thr Pro Asn Ser Leu Leu Val Ser Trp Gln Pro Pro Arg Ala
                195                 200                 205

Arg Ile Thr Gly Tyr Ile Ile Lys Tyr Glu Lys Pro Gly Ser Pro Pro
210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr Asp
                260                 265                 270

Glu Leu Pro Gln Leu Val Thr Leu Pro His Pro Asn Leu His Gly Pro
                275                 280                 285

Glu Ile Leu Asp Val Pro Ser Thr
290                 295

<210> SEQ ID NO 5
<211> LENGTH: 549
<212> TYPE: PRT
<213> ORGANISM: Artificial Sequence
<220> FEATURE:
<223> OTHER INFORMATION: Description of Artificial Sequence: Fibronectin
      fragment named CH-271

<400> SEQUENCE: 5

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
                35                  40                  45

Pro Ser Asp Asn Ala Val Val Leu Thr Asn Leu Leu Pro Gly Thr Glu
            50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
```

```
                195                 200                 205
Tyr Arg Ile Thr Tyr Gly Glu Thr Gly Gly Asn Ser Pro Val Gln Glu
210                 215                 220
Phe Thr Val Pro Gly Ser Lys Ser Thr Ala Thr Ile Ser Gly Leu Lys
225                 230                 235                 240
Pro Gly Val Asp Tyr Thr Ile Thr Val Tyr Ala Val Thr Gly Arg Gly
                245                 250                 255
Asp Ser Pro Ala Ser Ser Lys Pro Ile Ser Ile Asn Tyr Arg Thr Glu
            260                 265                 270
Ile Asp Lys Pro Ser Met Ala Ile Pro Ala Pro Thr Asp Leu Lys Phe
        275                 280                 285
Thr Gln Val Thr Pro Thr Ser Leu Ser Ala Gln Trp Thr Pro Pro Asn
    290                 295                 300
Val Gln Leu Thr Gly Tyr Arg Val Arg Val Thr Pro Lys Glu Lys Thr
305                 310                 315                 320
Gly Pro Met Lys Glu Ile Asn Leu Ala Pro Asp Ser Ser Ser Val Val
                325                 330                 335
Val Ser Gly Leu Met Val Ala Thr Lys Tyr Glu Val Ser Val Tyr Ala
            340                 345                 350
Leu Lys Asp Thr Leu Thr Ser Arg Pro Ala Gln Gly Val Val Thr Thr
        355                 360                 365
Leu Glu Asn Val Ser Pro Pro Arg Arg Ala Arg Val Thr Asp Ala Thr
    370                 375                 380
Glu Thr Thr Ile Thr Ile Ser Trp Arg Thr Lys Thr Glu Thr Ile Thr
385                 390                 395                 400
Gly Phe Gln Val Asp Ala Val Pro Ala Asn Gly Gln Thr Pro Ile Gln
                405                 410                 415
Arg Thr Ile Lys Pro Asp Val Arg Ser Tyr Thr Ile Thr Gly Leu Gln
            420                 425                 430
Pro Gly Thr Asp Tyr Lys Ile Tyr Leu Tyr Thr Leu Asn Asp Asn Ala
        435                 440                 445
Arg Ser Ser Pro Val Val Ile Asp Ala Ser Thr Ala Ile Asp Ala Pro
    450                 455                 460
Ser Asn Leu Arg Phe Leu Ala Thr Thr Pro Asn Ser Leu Leu Val Ser
465                 470                 475                 480
Trp Gln Pro Pro Arg Ala Arg Ile Thr Gly Tyr Ile Ile Lys Tyr Glu
                485                 490                 495
Lys Pro Gly Ser Pro Pro Arg Glu Val Val Pro Arg Pro Arg Pro Gly
            500                 505                 510
Val Thr Glu Ala Thr Ile Thr Gly Leu Glu Pro Gly Thr Glu Tyr Thr
        515                 520                 525
Ile Tyr Val Ile Ala Leu Lys Asn Asn Gln Lys Ser Glu Pro Leu Ile
    530                 535                 540
Gly Arg Lys Lys Thr
545

<210> SEQ ID NO 6
<211> LENGTH: 574
<212> TYPE: PRT
<213> ORGANISM: Artificial Sequence
<220> FEATURE:
<223> OTHER INFORMATION: Description of Artificial Sequence: Fibronectin
      fragment named CH-296

<400> SEQUENCE: 6

Pro Thr Asp Leu Arg Phe Thr Asn Ile Gly Pro Asp Thr Met Arg Val
```

```
              1               5              10              15
Thr Trp Ala Pro Pro Ser Ile Asp Leu Thr Asn Phe Leu Val Arg
             20                  25                  30

Tyr Ser Pro Val Lys Asn Glu Glu Asp Val Ala Glu Leu Ser Ile Ser
             35                  40                  45

Pro Ser Asp Asn Ala Val Val Leu Thr Asn Leu Leu Pro Gly Thr Glu
             50                  55                  60

Tyr Val Val Ser Val Ser Ser Val Tyr Glu Gln His Glu Ser Thr Pro
 65                      70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
                130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
                195                 200                 205

Tyr Arg Ile Thr Tyr Gly Glu Thr Gly Gly Asn Ser Pro Val Gln Glu
210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp Lys Pro Ser Met Ala Ile Pro Ala Pro Thr Asp Leu Lys Phe
                275                 280                 285

Thr Gln Val Thr Pro Thr Ser Leu Ser Ala Gln Trp Thr Pro Pro Asn
                290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
                340                 345                 350

Leu Lys Asp Thr Leu Thr Ser Arg Pro Ala Gln Gly Val Val Thr Thr
                355                 360                 365

Leu Glu Asn Val Ser Pro Pro Arg Arg Ala Arg Val Thr Asp Ala Thr
                370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
                420                 425                 430
```

-continued

Pro Gly Thr Asp Tyr Lys Ile Tyr Leu Tyr Thr Leu Asn Asp Asn Ala
    435                 440                 445

Arg Ser Ser Pro Val Val Ile Asp Ala Ser Thr Ala Ile Asp Ala Pro
450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
                500                 505                 510

Val Thr Glu Ala Thr Ile Thr Gly Leu Glu Pro Gly Thr Glu Tyr Thr
    515                 520                 525

Ile Tyr Val Ile Ala Leu Lys Asn Asn Gln Lys Ser Glu Pro Leu Ile
    530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
                565                 570

<210> SEQ ID NO 7
<211> LENGTH: 302
<212> TYPE: PRT
<213> ORGANISM: Artificial Sequence
<220> FEATURE:
<223> OTHER INFORMATION: Description of Artificial Sequence: Fibronectin
      fragment named C-CS1

<400> SEQUENCE: 7

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Asp Glu Leu Pro Gln Leu Val Thr Leu Pro His
        275                 280                 285

Pro Asn Leu His Gly Pro Glu Ile Leu Asp Val Pro Ser Thr
    290                 295                 300

<210> SEQ ID NO 8
<211> LENGTH: 367
<212> TYPE: PRT
<213> ORGANISM: Artificial Sequence
<220> FEATURE:
<223> OTHER INFORMATION: Description of Artificial Sequence: Fibronectin
      fragment named CHV-89

<400> SEQUENCE: 8

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Pro Arg Arg Ala Arg Val
        275                 280                 285

```
Thr Asp Ala Thr Glu Thr Thr Ile Thr Ile Ser Trp Arg Thr Lys Thr
    290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

Thr Gly Leu Gln Pro Gly Thr Asp Tyr Lys Ile Tyr Leu Tyr Thr Leu
                340                 345                 350

Asn Asp Asn Ala Arg Ser Ser Pro Val Val Ile Asp Ala Ser Thr
                355                 360                 365
```

<210> SEQ ID NO 9
<211> LENGTH: 368
<212> TYPE: PRT
<213> ORGANISM: Artificial Sequence
<220> FEATURE:
<223> OTHER INFORMATION: Description of Artificial Sequence: Fibronectin fragment named CHV-90

<400> SEQUENCE: 9

```
Pro Thr Asp Leu Arg Phe Thr Asn Ile Gly Pro Asp Thr Met Arg Val
  1               5                  10                  15

Thr Trp Ala Pro Pro Ser Ile Asp Leu Thr Asn Phe Leu Val Arg
               20                  25                  30

Tyr Ser Pro Val Lys Asn Glu Glu Asp Val Ala Glu Leu Ser Ile Ser
               35                  40                  45

Pro Ser Asp Asn Ala Val Val Leu Thr Asn Leu Leu Pro Gly Thr Glu
  50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
               100                 105                 110

Arg Ala Thr Ile Thr Gly Tyr Arg Ile Arg His His Pro Glu His Phe
               115                 120                 125

Ser Gly Arg Pro Arg Glu Asp Arg Val Pro His Ser Arg Asn Ser Ile
               130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
                195                 200                 205

Tyr Arg Ile Thr Tyr Gly Glu Thr Gly Gly Asn Ser Pro Val Gln Glu
                210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp Lys Pro Ser Met Ala Ile Asp Ala Pro Ser Asn Leu Arg Phe
                275                 280                 285
```

-continued

```
Leu Ala Thr Thr Pro Asn Ser Leu Leu Val Ser Trp Gln Pro Pro Arg
        290                 295                 300

Ala Arg Ile Thr Gly Tyr Ile Ile Lys Tyr Glu Lys Pro Gly Ser Pro
305                 310                 315                 320

Pro Arg Glu Val Val Pro Arg Pro Arg Pro Gly Val Thr Glu Ala Thr
                325                 330                 335

Ile Thr Gly Leu Glu Pro Gly Thr Glu Tyr Thr Ile Tyr Val Ile Ala
            340                 345                 350

Leu Lys Asn Asn Gln Lys Ser Glu Pro Leu Ile Gly Arg Lys Lys Thr
        355                 360                 365

<210> SEQ ID NO 10
<211> LENGTH: 370
<212> TYPE: PRT
<213> ORGANISM: Artificial Sequence
<220> FEATURE:
<223> OTHER INFORMATION: Description of Artificial Sequence: Fibronectin
      fragment named CHV-92

<400> SEQUENCE: 10

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
        50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285
```

```
Thr Gln Val Thr Pro Thr Ser Leu Ser Ala Gln Trp Thr Pro Pro Asn
        290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
                340                 345                 350

Leu Lys Asp Thr Leu Thr Ser Arg Pro Ala Gln Gly Val Val Thr Thr
                355                 360                 365

Leu Glu
    370

<210> SEQ ID NO 11
<211> LENGTH: 457
<212> TYPE: PRT
<213> ORGANISM: Artificial Sequence
<220> FEATURE:
<223> OTHER INFORMATION: Description of Artificial Sequence: Fibronectin
      fragment named CHV-179

<400> SEQUENCE: 11

Pro Thr Asp Leu Arg Phe Thr Asn Ile Gly Pro Asp Thr Met Arg Val
  1               5                  10                  15

Thr Trp Ala Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
                35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
                195                 200                 205

Tyr Arg Ile Thr Tyr Gly Glu Thr Gly Gly Asn Ser Pro Val Gln Glu
                210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
    260                 265                 270
```

```
Ile Asp Lys Pro Ser Met Asn Val Ser Pro Pro Arg Arg Ala Arg Val
        275                 280                 285

Thr Asp Ala Thr Glu Thr Thr Ile Thr Ile Ser Trp Arg Thr Lys Thr
    290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

Thr Gly Leu Gln Pro Gly Thr Asp Tyr Lys Ile Tyr Leu Tyr Thr Leu
            340                 345                 350

Asn Asp Asn Ala Arg Ser Ser Pro Val Val Ile Asp Ala Ser Thr Ala
        355                 360                 365

Ile Asp Ala Pro Ser Asn Leu Arg Phe Leu Ala Thr Thr Pro Asn Ser
    370                 375                 380

Leu Leu Val Ser Trp Gln Pro Pro Arg Ala Arg Ile Thr Gly Tyr Ile
385                 390                 395                 400

Ile Lys Tyr Glu Lys Pro Gly Ser Pro Pro Arg Glu Val Val Pro Arg
                405                 410                 415

Pro Arg Pro Gly Val Thr Glu Ala Thr Ile Thr Gly Leu Glu Pro Gly
            420                 425                 430

Thr Glu Tyr Thr Ile Tyr Val Ile Ala Leu Lys Asn Asn Gln Lys Ser
        435                 440                 445

Glu Pro Leu Ile Gly Arg Lys Lys Thr
    450                 455

<210> SEQ ID NO 12
<211> LENGTH: 472
<212> TYPE: PRT
<213> ORGANISM: Artificial Sequence
<220> FEATURE:
<223> OTHER INFORMATION: Description of Artificial Sequence: Fibronectin
      fragment named CHV-181

<400> SEQUENCE: 12

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175
```

```
Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
            355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
    450                 455                 460

Ser Asn Leu Arg Phe Leu Ala Thr
465                 470

<210> SEQ ID NO 13
<211> LENGTH: 276
<212> TYPE: PRT
<213> ORGANISM: Artificial Sequence
<220> FEATURE:
<223> OTHER INFORMATION: Description of Artificial Sequence: Fibronectin
      fragment named H-275-Cys

<400> SEQUENCE: 13

Met Ala Ala Ser Ala Ile Pro Ala Pro Thr Asp Leu Lys Phe Thr Gln
1               5                   10                  15

Val Thr Pro Thr Ser Leu Ser Ala Gln Trp Thr Pro Pro Asn Val Gln
            20                  25                  30

Leu Thr Gly Tyr Arg Val Arg Val Thr Pro Lys Glu Lys Thr Gly Pro
        35                  40                  45

Met Lys Glu Ile Asn Leu Ala Pro Asp Ser Ser Ser Val Val Val Ser
    50                  55                  60
```

-continued

Gly Leu Met Val Ala Thr Lys Tyr Glu Val Ser Val Tyr Ala Leu Lys
 65                  70                  75                  80

Asp Thr Leu Thr Ser Arg Pro Ala Gln Gly Val Val Thr Thr Leu Glu
                 85                  90                  95

Asn Val Ser Pro Pro Arg Arg Ala Arg Val Thr Asp Ala Thr Glu Thr
            100                 105                 110

Thr Ile Thr Ile Ser Trp Arg Thr Lys Thr Glu Thr Ile Thr Gly Phe
        115                 120                 125

Gln Val Asp Ala Val Pro Ala Asn Gly Gln Thr Pro Ile Gln Arg Thr
    130                 135                 140

Ile Lys Pro Asp Val Arg Ser Tyr Thr Ile Thr Gly Leu Gln Pro Gly
145                 150                 155                 160

Thr Asp Tyr Lys Ile Tyr Leu Tyr Thr Leu Asn Asp Asn Ala Arg Ser
                165                 170                 175

Ser Pro Val Val Ile Asp Ala Ser Thr Ala Ile Asp Ala Pro Ser Asn
            180                 185                 190

Leu Arg Phe Leu Ala Thr Thr Pro Asn Ser Leu Leu Val Ser Trp Gln
        195                 200                 205

Pro Pro Arg Ala Arg Ile Thr Gly Tyr Ile Ile Lys Tyr Glu Lys Pro
    210                 215                 220

Gly Ser Pro Pro Arg Glu Val Val Pro Arg Pro Arg Pro Gly Val Thr
225                 230                 235                 240

Glu Ala Thr Ile Thr Gly Leu Glu Pro Gly Thr Glu Tyr Thr Ile Tyr
                245                 250                 255

Val Ile Ala Leu Lys Asn Asn Gln Lys Ser Glu Pro Leu Ile Gly Arg
            260                 265                 270

Lys Lys Thr Cys
        275

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Primer 12S

<400> SEQUENCE: 14
aaaccatggc agctagcgct attcctgcac caactgac                              38

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Primer 14A

<400> SEQUENCE: 15
aaaggatccc taactagtct ttttccttcc aatcag                                36

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Primer
      Cys-A

<400> SEQUENCE: 16
aaaagcggcc gctagcgcaa gccatggtct gtttcctgtg                            40

```
<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Primer
      Cys-S

<400> SEQUENCE: 17
aaaagcggcc gcactagtgc atagggatcc ggctgagcaa c                           41

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Designed
      peptide based on matrix-protein derived from
      influenza virus

<400> SEQUENCE: 18

Gly Ile Leu Gly Phe Val Phe Thr Leu
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Designed
      peptide based on HLA A2.1 binding peptide derived
      from melanoma antigen MAGE3

<400> SEQUENCE: 19

Phe Leu Trp Gly Pro Arg Ala Leu Val
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Designed
      peptide based on HLA A2.1 binding peptide derived
      from melanoma antigen MART1

<400> SEQUENCE: 20

Ala Ala Gly Ile Gly Ile Leu Thr Val
 1               5
```

METHOD OF EXTENDED CULTURE FOR ANTIGEN-SPECIFIC CYTOTOXIC LYMPHOCYTES

The present application is the national stage of PCT Application No. PCT/JP02/08298, which was filed on Aug. 15, 2002. PCT Application No. PCT/JP02/08298 claims the benefit of priority of JP 2002-084428, which was filed on Mar. 25, 2002, JP 2001-376966, which was filed on Dec. 11, 2001, and JP 2001-246747, which was filed on Aug. 15, 2001.

TECHNICAL FIELD

The present invention relates to methods for inducing, maintaining and expanding cytotoxic T cell having an antigen-specific cytotoxic activity, which is useful in the medical field.

BACKGROUND ART

A living body is protected from foreign substances mainly by an immune response, and an immune system has been established by various cells and the soluble factors produced thereby. Among them, leukocytes, especially lymphocytes, play a key role. The lymphocytes are classified in two major types, B lymphocyte (which may be hereinafter referred to as B cell) and T lymphocyte (which may be hereinafter referred to as T cell), both of which specifically recognize an antigen and act on the antigen to protect the living body.

T cell is subclassified to helper T cell having CD(Cluster Designation)4 marker (hereinafter referred to as $T_H$), mainly involved in assisting in antibody production and induction of various immune responses, and cytotoxic T cell having CD8 marker ($T_c$: cytotoxic T lymphocyte, also referred to as killer T cell, which may be hereinafter referred to as CTL), mainly exhibiting a cytotoxic activity. CTL, which plays the most important role in recognizing, destroying and eliminating tumor cell, virus-infected cell or the like, does not produce an antibody specifically reacting with an antigen like in B cell, but directly recognizes and acts on antigens (antigenic peptide) from a target cell which is associated with major histocompatibility complex (MHC, which may be also referred to as human leukocyte antigen (HLA) in human) Class I molecules existing on the surface of the target cell membrane. At this time, T cell receptor (hereinafter referred to as TCR) existing on the surface of the CTL membrane specifically recognizes the above-mentioned antigenic peptides and MHC Class I molecules, and determines whether the antigenic peptide is derived from itself or nonself. Target cell which has been determined to be from nonself is then specifically destroyed and eliminated by CTL.

Recent years, a therapy which would cause a heavier physical burden on a patient, such as pharmacotherapy and radiotherapy, has been reconsidered, and an interest has increased in an immunotherapy with a lighter physical burden on a patient. Especially, there has been remarked an effectiveness of adoptive immunotherapy in which CTL capable of specifically reacting with an antigen of interest is induced in vitro from CTL or T cell derived from a human having normal immune function, and then transferred to a patient. For instance, it has been suggested that adoptive immunotherapy using an animal model is an effective therapy for virus infection and tumor (authored by Greenberg, P. D., Advances in Immunology, published in 1992). Further, use of CTL to a patient with congenital, acquired or iatrogenic T cell immunodeficiency has been remarked, from the fact that administration of CTL to a patient with immunodeficiency results in reconstruction of specific CTL response, by which cytomegalovirus is rapidly and persistently eliminated without showing toxicity [Reusser P., et al., Blood, 78(5), 1373-1380 (1991)] and the like. In this therapy, it is important to maintain or increase the cell number with maintaining or enhancing the antigen-specific cytotoxic activity of the CTL.

Also, as to maintenance and increase of the cell number of CTL, if an effective cell number in adoptive immunotherapy for human is deduced on the basis of the studies on an animal model, it is thought that $10^9$ to $10^{10}$ antigen-specific T cells are necessary (authored by Greenberg, P. D., Advances in Immunology, published in 1992). In other words, in adoptive immunotherapy, it can be said that it is a major problem to obtain the above cell number in vitro in a short period of time.

As to maintenance and enhancement of an antigen-specific cytotoxic activity of CTL, there has been generally employed a method of repeating stimulation with an antigen of interest when a specific response to an antigen for CTL is induced. However, in this method, the cell number may temporarily be increased, but the cell number is eventually decreased, and necessary cell number cannot be obtained. As its countermeasure, there are no other means in the current situation but to lyophilize the cells in an earlier stage during repeat of stimulation with an antigen, or to obtain antigen-specific CTL clones, lyophilize a part of the clones, and repeat antigen stimulation to the lyophilized cells after thawing if the cell number or antigen-specific cytotoxic activity of the CTL clones is lowered due to a long-term culture.

A method for establishing T cell by a long-term culture using mouse T cell has been reported [Paul W. E. et al., Nature, 294(5843), 697-699 (1981)], which is a method for isolating T cell and establishing a cell strain therewith. However, it is impossible to proliferate T cell to $10^9$ to $10^{10}$ cells by this method. Next, U.S. Pat. No. 5,057,423 discloses a method comprising inducing lymphokine-activated killer (LAK) cell using a large amount of interleukin 2 (IL-2) in a high concentration, thereby increasing the cell number in 100 folds in 3 to 4 days. This cell number is enormous, considering that it usually takes about 24 hours for a single cell to be divided and proliferated into two cells. In addition, adoptive immunotherapy has been tried by inducing tumor-infiltrating lymphocyte (TIL) using IL-2 in a high concentration as above [Rosenberg S. A. et al, New Engl. J. Med., 313(23), 1485-1492 (1985); Rosenberg S. A. et al, New Engl. J. Med., 319 (25), 1676-1680 (1988); Ho M. et al., Blood, 81(8), 2093-2101 (1993)]. However, the former is a method for obtaining T cell which is non-specific for an antigen, and in the latter, antigen specificity is very low, if any, because activated polyclonal lymphocyte population is used. Further, in both of the above-mentioned methods, IL-2 is used in a high concentration in order to promote cell proliferation. It is reported that apoptosis (cell death) may occur when T cell treated with IL-2 in a high concentration is stimulated with a specific antigen in the absence of IL-2 [Lenardo M. J. et al., Nature, 353(6347), 858-861 (1991); Boehme S. A. et al., Eur. J. Immunol., 23(7), 1552-1560 (1993)]. Therefore, the effectiveness of LAK cell or TIL obtained by the above-mentioned methods is problematic.

In addition, when T cell is cultured at a low density ($5 \times 10^3$ to $1 \times 10^4$ cells/ml) in the presence of T-cell growth factor and IL-2, T cell rapidly proliferates over a period of 7 days, and eventually proliferates to a saturation density of 3 to $5 \times 10^5$ cells/ml. However, it is also reported that the cell always dies once the cell reaches the saturation density [Gillis S. et al., Immunol. Rev., 54, 81-109 (1981)]. Therefore, LAK cell, TIL and the method for culturing T cell at a low density are problematic in both aspects of actual use and usefulness.

Next, regarding the antigen-specific CTL, there are reported adoptive immunotherapy in which allogenic cytomegalovirus(CMV)-specific CTL is cultured in vitro for 5 to 12 weeks to proliferate CTL, and then administered intravenously to a patient with immunodeficiency [Riddell S. A. et al., *Science*, 257(5067), 238-240 (1992)]; and a method for isolating and expanding a CMV-specific CTL clone using self-CMV infected fibroblast and IL-2 [Riddell S. A. et al., *J. Immunol.*, 146(8), 2795-2804 (1991)] or using anti-CD3 monoclonal antibody (anti-CD3 mAb) and IL-2 [Riddell S. A. et al., *J. Immunol. Methods*, 128(2), 189-201 (1990)]. However, there is a serious problem in these methods. Specifically, it takes about 3 months to obtain $1\times10^9$ cells/ml of antigen-specific CTLs, during which time the symptoms of the patient advance, so that it is difficult to appropriately treat the disease depending on the situation.

As a method of solving the above-mentioned problem, WO 96/06929 discloses an REM method (rapid expansion method). This REM method is a method for expanding a primary T cell population containing antigen-specific CTL and $T_H$ in a short period of time. In other words, this method is characterized in that a large amount of T cell can be provided by expanding individual T cell clones. However, there is a problem as described below. In the REM method, antigen-specific CTL is expanded using anti-CD3 antibody, IL-2, and PBMC (peripheral blood mononuclear cell) made deficient in an ability for proliferation by irradiation, and Epstein-Barr virus (hereinafter simply referred to as EBV)-infected cells. However, there are problems that risk of admixing EBV-transformed B cell (EBV-B cell) into T cell is not deniable (problem in safety); that a large amount of PBMC (PBMC in an amount of about 40 times the number of antigen-specific CTL required) is required as feeder cell; that the antigen-specific cytotoxic activity of the expanded CTL cannot be sufficiently satisfactory; that the antigen-specific cytotoxic activity possessed by T cell is decreased with the cell proliferation when CTL is allowed to proliferate using a T cell population other than the T cell clone; and the like.

In other words, in a conventional method for preparing antigen-specific CTL, there have not been solved the problems essential to adoptive immunotherapy in which CTL having an antigen-specific cytotoxic activity effectively used in the treatment, is prepared in a sufficient amount for a short period of time.

DISCLOSURE OF INVENTION

An object of the present invention is to provide methods for inducing, maintaining and expanding CTL having an antigen-specific cytotoxic activity at a high level, which is suitably used in adoptive immunotherapy.

Concretely, the present invention relates to:
(1) a method for inducing cytotoxic T cell having an antigen-specific cytotoxic activity, characterized in that the method comprises the step of incubating a precursor cell capable of differentiating to cytotoxic T cell with an antigen presenting cell in the presence of at least one substance selected from the group consisting of:
(A) a substance having a binding activity to CD44;
(B) a substance capable of regulating a signal emitted by binding a CD44 ligand to CD44;
(C) a substance capable of inhibiting binding of a growth factor to a growth factor receptor;
(D) a substance capable of regulating a signal emitted by binding of a growth factor to a growth factor receptor; and
(E) fibronectin, a fragment thereof or a mixture thereof;

(2) the method according to the above (1), wherein the substance having a binding activity to CD44 is the CD44 ligand and/or an anti-CD44 antibody;
(3) the method according to the above (2), wherein the CD44 ligand is hyaluronic acid;
(4) the method according to the above (1), wherein the substance capable of inhibiting binding of a growth factor to a growth factor receptor is a substance having a binding activity to the growth factor;
(5) the method according to the above (4), wherein the substance having a binding activity to the growth factor is an anti-growth factor antibody;
(6) the method according to any one of the above (1), (4) and (5), wherein the growth factor is at least one growth factor selected from the group consisting of hepatocyte growth factor, insulin-like growth factor-1 and insulin-like growth factor-2;
(7) the method according to the above (1), wherein the fragment of the fibronectin is a fragment having at least one domain selected from the group consisting of:
(a) a VLA-4 binding domain,
(b) a VLA-5 binding domain, and
(c) a heparin binding domain;
(8) a method for maintaining cytotoxic T cell having an antigen-specific cytotoxic activity, characterized in that the method comprises the step of continuously culturing the cytotoxic T cell in the presence of at least one substance selected from the group consisting of (A) to (E) of the above (1);
(9) the method according to the above (8), wherein the substance having a binding activity to CD44 is the CD44 ligand and/or an anti-CD44 antibody;
(10) the method according to the above (9), wherein the CD44 ligand is hyaluronic acid;
(11) the method according to the above (8), wherein the substance capable of inhibiting binding of a growth factor to a growth factor receptor is a substance having a binding activity to the growth factor;
(12) the method according to the above (11), wherein the substance having a binding activity to the growth factor is an anti-growth factor antibody;
(13) the method according to any one of the above (8), (11) and (12), wherein the growth factor is at least one growth factor selected from the group consisting of hepatocyte growth factor, insulin-like growth factor-1 and insulin-like growth factor-2;
(14) the method according to the above (8), wherein the fragment of the fibronectin is a fragment having at least one domain selected from the group consisting of:
(a) a VLA-4 binding domain,
(b) a VLA-5 binding domain, and
(c) a heparin binding domain;
(15) a method for expanding cytotoxic T cell having an antigen-specific cytotoxic activity, characterized in that the method comprises the step of incubating the cytotoxic T cell in the presence of at least one substance selected from the group consisting of (A) to (E) of the above (1);
(16) the method according to the above (15), wherein the cytotoxic T cell is incubated further in the presence of anti-CD3 antibody in the above step;
(17) the method according to the above (15) or (16), wherein the cytotoxic T cell is incubated together with a feeder cell in the above step;
(18) the method according to the above (17), wherein the feeder cell is a non-virus-infected cell;

(19) the method according to any one of the above (15) to (18), wherein the substance having a binding activity to CD44 is the CD44 ligand and/or an anti-CD44 antibody;
(20) the method according to the above (19), wherein the CD44 ligand is hyaluronic acid;
(21) the method according to any one of the above (15) to (18), wherein the substance capable of inhibiting binding of a growth factor to a growth factor receptor is a substance having a binding activity to the growth factor;
(22) the method according to the above (21), wherein the substance having a binding activity to the growth factor is an anti-growth factor antibody;
(23) the method according to any one of the above (15) to (18), (21) and (22), wherein the growth factor is at least one growth factor selected from the group consisting of hepatocyte growth factor, insulin-like growth factor-1 and insulin-like growth factor-2;
(24) the method according to the above (15), wherein the fragment of the fibronectin is a fragment having at least one domain selected from the group consisting of:
(a) a VLA-4 binding domain,
(b) a VLA-5 binding domain, and
(c) a heparin binding domain;
(25) a method for collecting cytotoxic T cell, comprising the step of selecting a cell population rich in cytotoxic T cell having an antigen-specific cytotoxic activity from a culture containing the cytotoxic T cell obtained by the method of any one of the above (1) to (24);
(26) a cytotoxic T cell having an antigen-specific cytotoxic activity prepared by the method of any one of the above (1) to (25);
(27) a therapeutic agent, characterized in that the therapeutic agent comprises the cytotoxic T cell of the above (26) as an effective ingredient.

BEST MODE FOR CARRYING OUT THE INVENTION

Figure 1:
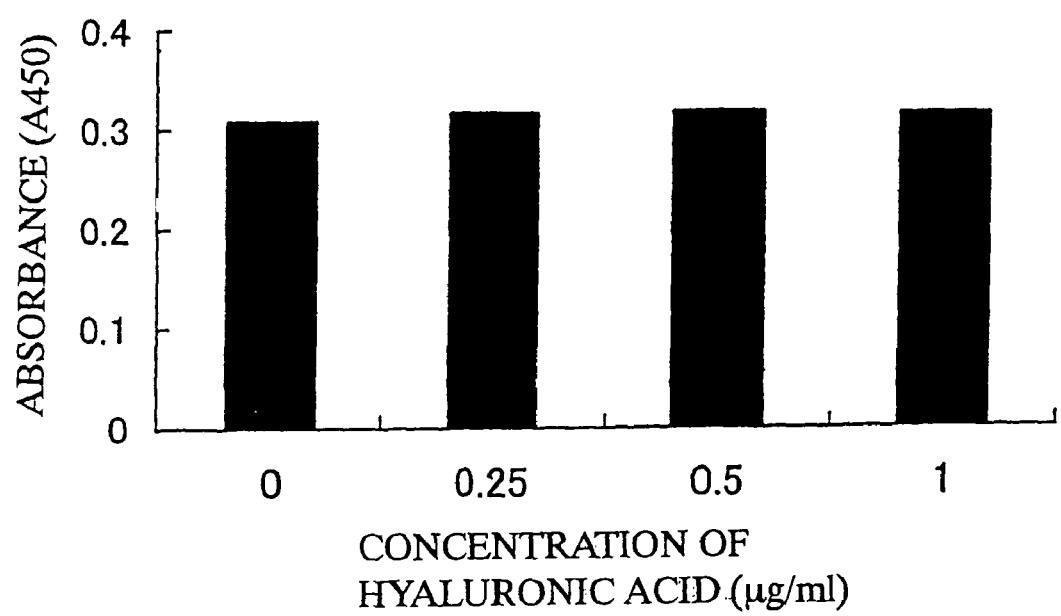
FIG. 1 is a graph showing an activity of hyaluronic acid to inhibit binding of a soluble CD44 and a soluble CD44-recognizing antibody.

It has been found that unexpectedly an ability (also referred to hereinafter as action) of maintaining or enhancing an antigen-specific cytotoxic activity of CTL is exhibited by at least one substance (the substance being used as an effective ingredient in the present invention) selected from the group consisting of the following (A) to (E):
(A) a substance having a binding activity to CD44;
(B) a substance capable of regulating a signal emitted by binding a CD44 ligand to CD44;
(C) a substance capable of inhibiting binding of a growth factor to a growth factor receptor;
(D) a substance capable of regulating a signal emitted by binding of a growth factor to a growth factor receptor; and
(E) fibronectin, a fragment thereof or a mixture thereof, and the present invention has been accomplished thereby.

Therefore, according to the present invention, there are provided methods for inducing, maintaining and expanding CTL having an antigen-specific cytotoxic activity at a high level, which is suitably used in adoptive immunotherapy.

The present invention will be explained concretely hereinbelow.

(1) Method for Inducing Cytotoxic T Cell of Present Invention

It has been known that CTL induced by antigen-presenting cell usually lowers its antigen-specific cytotoxic activity during the period of maintaining or proliferating CTL. According to the present invention, there is provided a method for inducing antigen-specific CTL which does not cause a marked lowering of the antigen-specific cytotoxic activity as conventionally observed, even when the cell after induction is maintained over a long period of time or proliferated.

One of the great features of the method for inducing CTL of the present invention resides in that CTL is induced in the presence of the above-mentioned effective ingredient. CTL is induced by incubating a precursor cell capable of differentiating to CTL with an appropriate antigen-presenting cell in the presence of the effective ingredient in order to give the CTL obtained an ability of recognizing the desired antigen. The precursor cell is not particularly limited, so long as the precursor cell is a cell which is in a stage before the cell becomes CTL and fated to differentiate to CTL, and includes, for instance, peripheral blood mononuclear cell (PBMC), naive cell, memory cell and the like. The antigen-presenting cell is not particularly limited, so long as the cell has an ability to present an antigen to be recognized to T cell. For instance, mononuclear cell, B cell, T cell, macrophage, dendritic cell, fibroblast or the like which is allowed to present a desired antigen can be used in the present invention.

The antigen-presenting cell can be prepared by adding an antigenic peptide to a cell having an antigen-presenting ability, thereby allowing the cell to present the antigenic peptide on its surface [see, for instance, Bednarek M. A. et al., *J. Immunol.* 147(12), 4047-4053 (1991)]. In addition, in the case where a cell having an antigen-presenting ability has an ability to process an antigen, an antigen is added to the cell, whereby the antigen is incorporated into the cell and processed therein, and fragmented antigenic peptides are presented on the cell surface. Incidentally, when an antigenic peptide is added to a cell having an antigen-presenting ability, an antigenic peptide matching the HLA restriction of the antigen-presenting cell used and the CTL to be induced are used.

Incidentally, the antigen used in the present invention is not particularly limited, and includes, for instance, exogenous antigens such as bacteria and viruses, endogenous antigens such as tumor-associated antigens (cancer antigens) and the like.

In the present invention, it is preferable that the antigen-presenting cell is made non-proliferative. In order to make the cell non-proliferative, for instance, the cell may be subjected to irradiation with X ray or the like, or a treatment with an agent such as mitomycin.

The medium used in the method for inducing CTL of the present invention is not particularly limited. There can be used known media prepared by blending components necessary for maintenance or growth of CTL, a precursor cell thereof and an antigen-presenting cell. The media may be, for instance, commercially available ones. These media may contain appropriate proteins, cytokines, and other components in addition to the originally contained constituents. Preferably, a medium containing interleukin-2 (IL-2) is used in the present invention. In addition, these proteins, cytokines and other components may be used by immobilizing them to a substrate such as a culture equipment or microbeads usable in the method of the present invention. Those components may be immobilized to the culture equipment or the like in an amount so as to give a desired effect by a known immobilization method which will be described later.

CD44 is a cell surface receptor widely existing in hematopoietic cells, fibroblasts, macrophages, and the like. Hyaluronic acid, heparan sulfate, chondroitin sulfate, osteopontin, type 1 collagen, type 4 collagen, fibronectin serglycin or the like has been reported as its ligands. As its function, there has been known to transduce a signal into cells through cell-cell adhesion or cell-extracellular matrix adhesion, thereby exhibiting functions such as activation of other adhesion molecules, and cytokine production. It has been known that CD44 also exists in CTL, and if hyaluronic acid or an anti-CD44 antibody binds to CD44, a tyrosine kinase domain existing in an intracellular region of CD44 is activated, thereby causing phosphorylation of tyrosine in an intracellular substrate protein, whereby intracellular signal transduction is carried out. In other words, it has been known that a signal is emitted by binding to CD44 its ligand or an anti-CD44 antibody, thereby leading to various functions.

In the present invention, the substance having a binding activity to CD44 is not particularly limited, so long as the substance exhibits an ability of maintaining or enhancing a specific cytotoxic activity of CTL. The substance is exemplified by, for instance, a CD44 ligand and/or an anti-CD44 antibody. The CD44 ligand is not particularly limited, so long as the ligand exhibits an ability of maintaining or enhancing a specific cytotoxic activity of CTL. The ligand includes, for instance, hyaluronic acid, heparan sulfate, chondroitin sulfate, osteopontin, type 1 collagen, type 4 collagen, fibronectin, serglycin and the like, and hyaluronic acid is especially preferable. In addition, the anti-CD44 antibody is not particularly limited, so long as the antibody exhibits an ability of maintaining or enhancing a specific cytotoxic activity of CTL. For instance, a commercially available anti-CD44 antibody can be used, and a derivative such as a fluorescence-labeled derivative can be used without particular limitation, so long as the derivative exhibits an ability of maintaining or enhancing a specific cytotoxic activity of CTL.

In the present invention, regardless of the presence or absence of the binding of CD44 to the substance having a binding activity to CD44, the desired effect can be obtained by regulating a signal emitted by binding of the CD44 ligand to CD44. In other words, the present invention can be carried out by using, as an effective ingredient, a substance capable of regulating a signal emitted by binding a CD44 ligand to CD44, in place of the substance having a binding activity to CD44. Here, the signal emitted by binding a CD44 ligand to CD44 also encompasses a signal emitted from a molecule of a living body receiving the signal. In other words, the signal includes, for instance, activation of a tyrosine kinase domain existing in an intracellular region of CD44, phosphorylation of tyrosine in an intracellular substrate protein by the above activated tyrosine kinase, and the like. A substance regulating these signals includes, for instance, various phosphokinases. In addition, the term "regulate or regulation" as used herein refers to transduce an activated signal to a downstream region in a signal transduction pathway, or to inhibit the transduction of the activated signal to a downstream region.

The term "growth factor" is a generic term of polypeptides promoting division or development of various cells. It has been known that the growth factor acts on a target cell via a specific receptor on cell membrane, and that most of the receptors of the growth factor activate tyrosine kinase domains existing in an intracellular region, thereby transducing a signal to a target cell.

In the present invention, the growth factor is not particularly limited, so long as the growth factor exhibits an ability of maintaining or enhancing a specific cytotoxic activity of CTL by inhibiting the binding of the growth factor to a growth factor receptor, or regulating a signal emitted by binding the growth factor to a growth factor receptor. The growth factor is exemplified by, for instance, hepatocyte growth factor (HGF), insulin-like growth factor-1 (IGF-1), insulin-like growth factor-2 (IGF-2), nerve growth factor (NGF), neurotrophic factor, epidermal growth factor, milk-derived growth factor, basic fibroblast growth factor (bFGF), brain-derived fibroblast growth factor, acidic fibroblast growth factor, keratinocyte growth factor, platelet-derived growth factor (PDGF), platelet basic protein, platelet fourth factor, connective tissue-activating peptide, colony-stimulating factor, erythropoietin, thrombopoietin, T cell growth factor, B cell growth factor, cartilage-derived factor, cartilage-derived growth factor, bone-derived growth factor, skeletal growth factor, epithelial cell growth factor, epithelial cell-derived growth factor, oculus-derived growth factor, testis-derived growth factor, Sertoli's cell-derived growth factor, mammotropic factor, spinal cord-derived growth factor, macrophage-derived growth factor, mesodermal growth factor, transforming growth factor-$\alpha$, transforming growth factor-$\beta$, heparin-binding EGF-like growth factor, amphyllegrin, smooth muscle cell-derived growth factor (SDGF), betacellulin, epiregulin, neuregulin-1, -2 and -3, vascular endothelial growth factor, neurotrophin, brain-derived neurotrophic factor (BDNF), neurotrophin (NT)-3, -4, -5, -6 and -7, glial cell line-derived neurotrophic factor, stem cell factor, midkine, pleiotrophin, ephrin, angiopoietin, activin, tumor necrosis factor, and the like. According to the present invention, preferred growth factors are exemplified by hepatocyte growth factor, insulin-like growth factor-1, and insulin-like growth factor-2.

HGF is a growth factor exhibiting proliferating action for hepatocytes, accelerating action for protein synthesis, ameliorating action for cholestasia, and further prophylactic action for renal disorders caused by drugs, and the like. As the HGF receptor, c-Met has been known, and all of various physiological actions of HGF are exhibited via c-Met. c-Met possesses a tyrosine kinase domain in its intracellular domain.

The insulin-like growth factor (IGF) is an insulin-like active substance which cannot be neutralized with an insulin antibody. There have been known the existence of two kinds of IGF, IGF-1 and IGF-2. The receptor to which IGF binds includes an insulin receptor, IGF-1 receptor and IGF-2 receptor, and especially the insulin receptor and IGF-1 receptor have a tyrosine kinase domain in their intracellular domain.

In the present invention, the substance capable of inhibiting the binding of the growth factor to its growth factor receptor is not particularly limited, so long as the substance exhibits an ability of maintaining or enhancing a specific cytotoxic activity of CTL. The substance includes a substance having a binding activity to the growth factor, and forming a complex with the growth factor, thereby inhibiting the binding of the growth factor to its growth factor receptor, or a substance having a binding activity to a growth factor receptor, thereby inhibiting the binding of the growth factor to the growth factor receptor. The former includes, for instance, an anti-growth factor antibody, preferably an anti-HGF antibody, an anti-IGF-1 antibody and an anti-IGF-2 antibody. The latter includes, for instance, an anti-growth factor receptor antibody, preferably an anti-c-Met antibody, an anti-insulin receptor antibody, an anti-IGF-1 receptor antibody and an anti-IGF-2 receptor antibody.

In addition, in the present invention, regardless of the presence or absence of the binding of the growth factor to a growth factor receptor, the desired effect can be obtained by regulating a signal emitted by binding the growth factor to a growth factor receptor. In other words, the present invention can also be carried out by using as an effective ingredient a substance capable of regulating a signal emitted by binding the growth factor to a growth factor receptor, in place of the substance capable of inhibiting the binding of the growth factor to a growth factor receptor. Here, the signal emitted by binding the growth factor to a growth factor encompasses a signal emitted from a molecule of a living body receiving the signal. The signal includes, for instance, activation of a tyrosine kinase domain existing in an intracellular region of the growth factor, phosphorylation of tyrosine in an intracellular substrate protein by tyrosine kinase, and the like. The substance for regulating these signals includes, for instance, a kinase inhibitor and the like.

The fibronectin and a fragment thereof as mentioned herein may be those obtained from nature, or those artificially synthesized by using a conventional genetic recombination technique or the like. The fibronectin and a fragment thereof can be prepared in a substantially pure form from a substance of natural origin, on the basis of the disclosure of Ruoslahti E. et al. [*J. Biol. Chem.*, 256(14), 7277-7281 (1981)]. The term "substantially pure fibronectin or fibronectin fragment" as referred to herein means that these fibronectin and fibronectin fragment do not substantially contain other proteins and the like originated from its source and co-existing with fibronectin in nature. Each of the above-mentioned fibronectin and a fragment thereof can be used in the present invention alone or in admixture of plural kinds.

The useful information relating to the fibronectin fragments which can be used in the present invention and the preparation of the fragments can be obtained from Kimizuka F., et al. [*J. Biochem.*, 110(2), 284-291 (1991)], Kornblihtt A. R. et al. [*EMBO J.*, 4(7), 1755-1759 (1985)], Sekiguchi K., et al [*Biochemistry*, 25(17), 4936-4941 (1986), and the like.

Fibronectin is a gigantic glycoprotein having a molecular weight of from 220 to 250 kD and binding to many of macromolecules of a living body, such as collagen, heparin, fibrin, integrin families VLA-4 and VLA-5, cells and microorganisms. Also, the fibronectin molecule is divided into some domain structures as its functional regions (*Taisha (Metabolism)*, 23(11) (1986)). A domain 1 has a molecular weight of about 30000 and binds to heparin, fibrin, *Staphylococcus aureus* or the like. A domain 2 has a molecular weight of about 40000 and binds to collagen. A domain 3 has a molecular weight of about 20000, and is considered to bind weakly to fibrin. A domain 4 has a molecular weight of about 75000 and is a cell-binding domain. A domain 5 (heparin-binding domain) has a molecular weight of about 35000 and binds strongly to heparin. A domain 6 has a molecular weight of about 30000 and binds to fibrin. A domain 7 is a carboxyl-terminal domain having a molecular weight of about 3,000. The domain 4 contains a VLA-5-binding domain and contains a VLA-4-binding domain between the domains 5 and 6. Also, there has been known that fibronectin has 3 modules of ED-A, ED-B and IIICS, and selective splicing is performed therefor. Further, IIICS has CS-1 and CS-5, each having a cell adhesion activity (*FIBRONECTIN*, Edited by Deane F. Mosher, ACADEMIC PRESS, INC. (1989)).

In the present invention, the fibronectin fragment is preferably, but not particularly limited to, for instance, a fragment having a region selected from the domains 1 to 7, VLA-4-binding domain, VLA-5-binding domain, ED-A, ED-B, IIICS, CS-1 and CS-5. In addition, the fibronectin fragment used in the present invention is preferably, but not particularly limited to, a fragment of from 1 to 200 kD, more preferably from 5 to 190 kD, even more preferably from 10 to 180 kD.

In the present invention, as the especially preferred fibronectin fragment, a fragment having at least one domain selected from the group consisting of (a) an integrin α5β1 (VLA-5)-binding domain as a cell-binding domain derived from fibronectin; (b) an integrin α4β1 (VLA-4)-binding domain; and (c) a heparin-binding domain is preferably used. For instance, the fragment comprising the VLA-5-binding domain includes a fragment having the amino acid sequence shown in SEQ ID NO: 1; the fragment comprising the VLA-4-binding domain includes a fragment having the amino acid sequence shown in SEQ ID NO: 2; and the fragment comprising the heparin-binding domain includes a fragment having the amino acid sequence shown in SEQ ID NO: 3, respectively.

The fragment preferably used in the present invention may have substitution, deletion, insertion or addition of one or more amino acids in an amino acid sequence derived from fibronectin within the range in which the fragment has the above-mentioned binding activity. For instance, a fragment having one or more amino acids inserted as a linker between two different domains can also be used in the present invention.

The substantially pure fibronectin fragment as referred to herein can also be prepared from a genetic recombinant on the basis of the description of e.g. U.S. Pat. No. 5,198,423. In particular, recombinant fragments referred to as H-271 (SEQ ID NO: 3), H-296 (SEQ ID NO: 4), CH-271 (SEQ ID NO: 5) and CH-296 (SEQ ID NO: 6) in Examples set forth below and a method of preparing these recombinant fragments are described in detail in this patent. In addition, a C-274 fragment (SEQ ID NO: 1) used in Examples set forth below can be obtained in accordance with the method described in U.S. Pat. No. 5,102,988. Further, a C-CS1 fragment (SEQ ID NO: 7) can be obtained in accordance with the method described in Japanese Patent Gazette No. 3104178.

Each of the above-mentioned fragments CH-271, CH-296, C-274 and C-CS1 is a polypeptide having a cell-binding domain having a binding activity to VLA-5. Also, C-CS1, H-296 or CH-296 is a polypeptide having a cell-binding domain having a binding activity to VLA-4. Further, H-271, H-296, CH-271 or CH-296 is a polypeptide having a heparin-binding domain.

A fragment in which each of the above domains is modified can also be used in the present invention. The heparin-binding site of fibronectin is constituted by three type III analogous sequences (III-12, III-13 and III-14). A fragment containing a heparin-binding site having deletion of one or two of the type III analogous sequences can also be used in the present invention. For instance, the fragments may be exemplified by CHV-89 (SEQ ID NO: 8), CHV-90 (SEQ ID NO: 9) or CHV-92 (SEQ ID NO: 10), which is a fragment in which a cell-binding site of fibronectin (VLA-5-binding domain: Pro1239 to Ser1515) and one of the III type analogous sequences are bound, or CHV-179 (SEQ ID NO: 11) or CHV-181 (SEQ ID NO: 12), which is a fragment in which the cell-binding site of fibronectin and two of the type III analogous sequences are bound. CHV-89, CHV-90 and CHV-92 contain III-13, III-14 and III-12, respectively; CHV-179 contains III-13 and III-14, and CHV-181 contains III-12 and III-13, respectively. CHV-89, CHV-90 and CHV-179 can be obtained in accordance with the method described in Japanese Patent Gazette No. 2729712. CHV-181 can be obtained in accordance with the method described in WO 97/18318. Further, CHV-92 can be obtained by genetic engineering technique using a plasmid constructed in a usual manner on the basis of the plasmid described in the above literature.

In addition, an H-275-Cys (SEQ ID NO: 13) used in Examples set forth below is a fragment having a heparin-binding domain of fibronectin and a C-terminal cysteine residue. This fragment can also be used in the present invention.

These fragments or their derived fragments obtained in a usual manner can be prepared by using microorganisms deposited to the International Patent Organism Depositary, National Institute of Advanced Industrial Science and Technology (formerly the Ministry of International Trade and Industry, National Institute of Bioscience and Human-Technology, Agency of Industrial Science and Technology), Tsukuba Central 6, 1-1, Higashi 1-chome Tsukuba-shi, Ibaraki-ken, Japan (Zip code 305-8566) under the following accession numbers, or by modifying a plasmid carried in each microorganism in accordance with a known method (for instance, site-directed mutagenesis).

FERM-BP-2799 (*Escherichia coli* carrying a plasmid encoding H-271)
International Date of Deposit: May 12, 1989;
FERM-BP-2800 (*Escherichia coli* carrying a plasmid encoding CH-296)
International Date of Deposit: May 12, 1989;
FERM-BP-5723 (*Escherichia coli* carrying a plasmid encoding C-CS1)
Original Date of Deposit: Mar. 5, 1990,
Date of Transfer to International Deposit: Oct. 23, 1996;
FERM P-10721 (*Escherichia coli* carrying a plasmid encoding H-296)
Japanese National Date of Deposit: May 12, 1989;
FERM P-12182 (*Escherichia coli* carrying a plasmid encoding CHV-89)
Japanese National Date of Deposit: Apr. 8, 1991; and
FERM P-12183 (*Escherichia coli* carrying a plasmid encoding CHV-179)
Japanese National Date of Deposit: Apr. 8, 1991.

The binding of the cell-binding domain of the fragment used in the present invention to a cell can be assayed by using a conventional method. For instance, such methods include a method of Williams D. A. et al. [*Nature*, 352(6334), 438-441 (1991)]. This method is a method of determining the binding of a cell to a fragment immobilized to a culture plate.

Also, the heparin-binding domain of the fragment can be evaluated in the same manner as above by using a heparin, for instance, a labeled heparin, in place of the cell in the above method.

As described above, since the fibronectin is a gigantic molecule, in the present invention, a fibronectin fragment is preferably used, from the viewpoint of convenience in use. When the fibronectin or a fragment thereof usable in the present invention is a product obtained from plasma or organs derived from an animal, since careful attention should be paid to contamination with animal-derived viruses (HCV, HIV and the like), purity and homogeneity, it is especially preferable that the fibronectin or a fragment thereof obtained by a genetic engineering technique as described above is preferably used.

The effective ingredient usable in the present invention can be used alone or in admixture of two or more kinds.

In the present invention, common conditions for incubating a precursor cell capable of differentiating to CTL together with an antigen-presenting cell (co-culturing) to induce CTL may be known conditions [see, for instance, Bednarek M. A. et al., *J. Immunol.*, 147(12), 4047-4053 (1991)]. The conditions for co-culturing are not particularly limited, and the conditions usually used for cell culturing can be used. For instance, the cells can be cultured under the conditions of 37° C. in the presence of 5% $CO_2$, and the like. The co-culture is usually carried out for about 2 to about 15 days, during which time the antigen-presenting cell may be exchanged with freshly prepared one for restimulation. In addition, the medium can be exchanged with a fresh one at appropriate time intervals.

The content of the effective ingredient of the present invention in the medium used for the co-culture is not particularly limited, so long as the desired effect can be obtained. The content of the effective ingredient is preferably from 0.001 to 1000 μg/ml, more preferably from 0.01 to 100 μg/ml. The expression "contain(ing) components such as effective ingredients in a medium" as used herein is intended to encompass an embodiment of immobilizing the components to a substrate such as a culture equipment into which a medium is introduced during cell culture, or microbeads which are used by introducing them into a medium, and contacting the substrate with the medium in order to contain the above components in the medium (regardless of whether or not the components remain immobilized to the substrate after contacting with the medium). It is desired that the effective ingredient is present by dissolving the effective component in the medium or immobilizing the effective component to the substrate such as a culture equipment or microbeads. In addition, the above effective ingredient preferably includes at least one member selected from the group consisting of hyaluronic acid, an anti-CD44 antibody, an anti-HGF antibody, an anti-IGF-1 antibody, an anti-IGF-2 antibody, and a fibronectin fragment.

The CTL thus induced has an ability of specifically recognizing the desired antigen, for instance, specifically destroying a cell having the antigen by its cytotoxic activity. This cytotoxic activity of CTL can be evaluated by a known method. For instance, the cytotoxic activity can be evaluated by determining cytotoxicity to a target cell labeled with the peptide presented by an antigen-presenting cell and a radioactive substance, a fluorescent substance or the like; an antigen-specific increase in CTL proliferation which can be determined by uptake of radioactivity; or the amount of cytokine such as GM-CSF or IFN-γ released antigen-specifically from CTL or target cell (see item (3) of Example 1-1 set forth below). Besides them, the cytotoxic activity can also be directly confirmed by using an antigenic peptide or complex labeled with a fluorescent pigment or the like. In this case, for instance, CTL is contacted with a first fluorescent marker coupled with a CTL specific antibody, and then with an antigenic peptide-MHC complex coupled with a second fluorescent marker, and the presence of a double-labeled cell is detected by FACS (fluorescence-activated cell sorting) analysis.

The CTL induced by the method of the present invention has an excellent property that the antigen-specific cytotoxic activity is not markedly lowered, as conventionally observed, even when the cell after induction is maintained or allowed to rapidly proliferate over a long period of time. Therefore, the induced CTL can be cloned, so that the CTL can also be maintained as a lymphocyte having a stable cytotoxic activity. For instance, the induced CTL can be allowed to proliferate and expanded by stimulating the CTL with an antigen, various cytokines or anti-CD3 antibodies. For the maintenance and the expansion of the CTL, a known method can be used without limitation. For instance, it is preferable to use the method for maintaining or the method for expanding cytotoxic T cell of the present invention described below.

(2) Method for Maintaining Cytotoxic T Cell of Present Invention

The method for maintaining cytotoxic T Cell of the present invention is a method for maintaining CTL with keeping its antigen-specific cytotoxic activity. One of the great features of the method resides in that CTL is continuously cultured in a medium containing the effective ingredient of the present invention, whereby the antigen-specific cytotoxic activity of the cell can be continuously maintained.

The CTL which can be applied to the above-mentioned method is not limited, and CTL obtained by a known method can be maintained by the method of the present invention, with keeping its antigen-specific cytotoxic activity. In addition, the method is also preferably used for maintaining CTL obtained by the method for inducing cytotoxic T cell of the present invention described in the above item (1).

In the present invention, common conditions for continuously culturing CTL may be in accordance with known conditions [see, for instance, Carter J. et al., *Immunology* 57(1), 123-129 (1986)]. The media used for the method for maintaining cytotoxic T cell of the present invention are not particularly limited, and for instance, the medium used for the above-mentioned method for inducing CTL can be used.

The method of the present invention is carried out by using a medium containing the above-mentioned effective ingredient. The content of the effective ingredient of the present invention in the medium for culturing is not particularly limited, so long as the desired effect can be obtained. The content of the effective ingredient is preferably from 0.001 to 1000 μg/ml, more preferably from 0.01 to 100 μg/ml. Incidentally, it is preferable that the effective ingredient is present in the medium by dissolving them in the medium, or immobilizing them to the substrate such as a culture equipment or microbeads. In addition, the above-mentioned effective ingredient is preferably at least one member selected from the group consisting of hyaluronic acid, an anti-CD44 antibody, an anti-HGF antibody, an anti-IGF-1 antibody, an anti-IGF-2 antibody, and a fibronectin fragment. Further, a cytokine or other known component can be added to the medium. In the present invention, a medium containing IL-2 is preferably used. In addition, these cytokine and other known components may be used by immobilizing them to the substrate such as a culture equipment or to microbeads in the same manner as above. The culture conditions are not particularly limited, and the conditions used for ordinary cell culture can be used. For instance, the cells can be cultured under the conditions at 37° C. in the presence of 5% $CO_2$, and the like. In addition, the medium can be exchanged with a fresh one at appropriate time intervals.

As described above, CTL can be maintained with suppressing lowering of its specific cytotoxic activity by continuously culturing CTL in a medium containing the effective ingredient of the present invention. The effects of the present invention described above can be confirmed by determining the cytotoxic activity possessed by CTL maintained by the method of the present invention according to the method described in item (3) of Example 1-1. In addition, the CTL maintained by the method can be allowed to proliferate by a known expanding method, and the CTL thus proliferated also maintains a specific cytotoxic activity. Incidentally, as a method for expanding CTL, the method for expanding CTL of the present invention described below can be preferably used.

(3) Method for Expanding Cytotoxic T Cell of Present Invention

Cytotoxic T cell is cultured under appropriate conditions, whereby the cell number can be increased (expansion). Conventionally, several methods for expanding CTL have been developed. As a method capable of efficiently proliferating CTL in a short period of time, the above-mentioned REM method developed by Riddell et al. has been known. This method uses PBMC made non-proliferative by X ray irradiation (used as feeder cell) and EBV-transformed B cell (EBV-B cell) and comprises culturing CTL in the presence of IL-2 and an anti-CD3 monoclonal antibody. However, this method has been problematic in that risk of admixing EBV-B cell into T cell is not deniable.

The method for expanding cytotoxic T cell of the present invention is a method capable of increasing the cell number with keeping its antigen-specific cytotoxic activity. The method is characterized by incubating (culturing) the cell in the presence of the above-mentioned effective ingredient of the present invention.

In the method of the present invention, CTL which can be applied to the method is not limited. The method can be suitably used for expansion of CTL having a cytotoxic activity obtained from a living body, CTL induced by a known method, CTL obtained by the method for inducing CTL of the present invention described in the above item (1), and CTL obtained by the method for maintaining CTL of the present invention described in the above item (2). Incidentally, in the present invention, common conditions for expanding CTL may be in accordance with known conditions [see, for instance, Uberti J. P. et al., *Clin. Immunol. Immunopathol.* 70(3), 234-240 (1994)].

In the method for expanding cytotoxic T cell of the present invention, it is desired that CTL is co-cultured in a medium further containing an anti-CD3 antibody, preferably an anti-CD3 monoclonal antibody, in addition to the above-mentioned effective ingredient. In addition, more preferably, CTL is co-cultured with appropriate feeder cell.

The medium used for the above-mentioned method is not particularly limited. A known medium prepared by blending components necessary for culture or growth of CTL can be used, and may be, for instance, commercially available ones. Incidentally, in the case where CTL is co-cultured with feeder cell, it is desired that the medium is suitable for maintenance and growth of both the CTL and the feeder cell. These media may contain appropriate proteins, cytokines and other components in addition to the originally contained constituents. For instance, a medium containing IL-2 is preferably used in the present invention. An anti-CD3 antibody, especially an anti-CD3 monoclonal antibody, can be added for the purpose of activating T cell receptor on CTL. Incidentally, the content of the anti-CD3 antibody in the medium may be determined according to the known conditions. For instance, the content is preferably from 0.01 to 400 μg/ml. Incidentally, these proteins, cytokines and other known components may be contained in the medium by dissolving them in the medium, or by immobilizing them to a substrate such as a culture equipment or microbeads.

The method for expanding CTL of the present invention is carried out by using a medium containing the above-mentioned effective ingredient. Incidentally, the above-mentioned effective ingredient is preferably at least one member selected from the group consisting of hyaluronic acid, an anti-CD44 antibody, an anti-HGF antibody, an anti-IGF-1 antibody, an anti-IGF-2 antibody, and a fibronectin fragment. In addition, the content of the effective ingredient of the present invention in the medium for culture is not particularly limited, so long as the desired effects can be obtained. The content of the effective ingredient is preferably from 0.001 to 1000 µg/ml, more preferably from 0.01 to 100 µg/ml. Incidentally, it is preferable that the effective ingredient is present in the medium by dissolving the effective ingredient in the medium, or by immobilizing the effective ingredient to the substrate such as a culture equipment or microbeads.

The feeder cell used for the method of the present invention is not particularly limited, so long as the feeder cell stimulates CTL cooperatively with an anti-CD3 antibody, especially an anti-CD3 monoclonal antibody, to activate T cell receptor or costimulatory signal receptor. In the present invention, for instance, PBMC or EBV-B cell is used. Usually, a feeder cell is used after its proliferating ability is taken away by means of irradiation or the like. Incidentally, the content of the feeder cell in the medium may be determined according to the known conditions. For instance, the content is preferably from $1\times10^5$ to $1\times10^7$ cells/ml.

In a particularly preferred embodiment of the present invention, non-virus-infected cell, for instance, a cell other than EBV-B cell, concretely self-derived or nonself-derived PBMC, is used as a feeder cell. By using the non-virus-infected cell, the possibility that EBV-B cell is admixed in an expanded CTL can be eliminated, thereby making it possible to increase the safety in medical treatments utilizing CTL, such as adoptive immunotherapy.

In the method for expanding CTL of the present invention, the conditions for culture are not particularly limited, and the conditions used for usual cell culture can be used. For instance, the cell can be cultured under the conditions of 37° C. in the presence of 5% $CO_2$, and the like. In addition, the medium can be exchanged with a fresh one at appropriate time intervals.

The method for expanding CTL of the present invention is not particularly limited to a certain method, so long as the effective ingredient of the present invention is added to the medium used in the method. The present invention encompasses an embodiment of adding the effective ingredient of the present invention to a medium in conventional methods for expanding CTL other than the above-mentioned method.

According to the method for expansion of the present invention, for instance, CTL of which cell number is increased $10^2$- to $10^3$-folds can be obtained by an expansion for 14 days. Further, CTL thus obtained has a higher antigen-specific cytotoxic activity, as compared to those obtained by a conventional method for expansion, for instance, the REM method.

The effects of the present invention as described above can be confirmed by determining the cytotoxic activity possessed by CTL expanded by the method of the present invention according to the method described in item (3) of Example 1-1.

In addition, the effective ingredient used in the present invention can be used as an agent for inducing CTL, an agent for maintaining CTL or an agent for expanding CTL (these agents are hereinafter referred to as an agent for culturing CTL), which acts for maintaining or enhancing an antigen-specific cytotoxic activity of CTL. The agent for culturing CTL may be the effective ingredient itself, or the agent for culturing CTL further comprises any other optional components, for instance, components necessary for culture or growth of CTL, feeder cell and the like, which are contained in the medium used in a method for inducing CTL, the medium used in a method for maintaining CTL or the medium used in a method for expanding CTL; appropriate proteins and cytokines (preferably IL-2); and other desired components. Also, a medium containing these agents for culturing CTL can be used as a medium for inducing, maintaining, or expanding CTL (a medium for CTL). In addition, these agents for culturing CTL may be mixed with the medium (including dissolving the agent), or may be immobilized to a substrate such as a culture equipment or microbeads. These media optionally contain the basic constituents for cell culture. Incidentally, the agents for culturing CTL and the media for CTL mentioned above can be prepared by appropriately mixing the desired components by known methods.

Further, according to the present invention, there can be provided substrates for inducing, maintaining or expanding CTL, in which the above-mentioned effective ingredient is immobilized to a substrate such as a given culture equipment (vessel) such as a culture plate, a petri dish, a flask or a bag, or a supporting carrier such as beads or membrane (more concretely the portion of the substrate contacting with the medium during the cell culture). The amount of the effective ingredient immobilized to the substrate is not particularly limited, so long as the desired effects of the present invention are obtained. When the CTL is induced or the like by using the substrate, it is preferable that the effective ingredient is in an amount that the effective ingredient can be contained in the given medium used for the substrate within the preferred range of the content of the effective ingredient in the medium as given in the explanation for the method for inducing CTL, method for maintaining CTL or method for expanding CTL of the present invention. In addition, in addition to the above-mentioned effective ingredient, the above-mentioned proteins, cytokines and other components may be optionally immobilized. The immobilization method is not particularly limited. For instance, there can be employed a known immobilization method such as protein adsorption, binding of biotin and avidin or streptoavidin, or chemical immobilization. The substrate is suitably used in the method for inducing CTL, method for maintaining CTL or method for expanding CTL of the present invention.

Usually, in the CTL-containing culture obtained by using the method for inducing CTL, the method for maintaining CTL and the method for expanding CTL as described above, cells other than CTL such as helper T cell are admixed therein. In the present invention, the cells in the culture are collected from the culture by centrifugation or the like, and the cells can be directly used as the CTL obtained by the method of the present invention.

In addition, a cell population (or a culture) rich in CTL having an antigen-specific cytotoxic activity can be further separated from the culture by a known method, and used as CTL obtained by the method of the present invention. Concretely, in the present invention, a cell population with a concentrated antigen-specific cytotoxic activity can be prepared by subjecting the culture to a separation procedure of CTL from cell other than the CTL (for instance, helper T cell) in the above-mentioned CTL-containing culture to use the cell population. The concentration of the antigen-specific cytotoxic activity by separating the above-mentioned cell population as described above could not have been accomplished by the conventional REM method. Therefore, as one embodiment of the present invention, there is provided a method for collecting cytotoxic T cell comprising the step of selecting a cell population rich in cytotoxic T cell having an antigen-specific cytotoxic activity from a CTL-containing culture obtained by any one of the method for inducing CTL, the method for maintaining CTL and the method for expanding CTL of the present invention. The method for collecting CTL of the present invention in a sense refers to a method of selectively obtaining a cell population of CTL having a high antigen-specific cytotoxic activity, and in a broad sense refers to a method for producing or acquiring a cell population of the CTL. The method of selecting the cell population is not particularly limited. For instance, the cell population rich in CTL can be obtained by selectively collecting only CTL from a CTL-containing culture obtained by using the method for inducing CTL, the method for maintaining CTL and the method for expanding CTL as described above, using magnetic beads or a column to which an antibody against a cell surface antigen expressed on the CTL cell surface, for instance, an anti-CD8 antibody, is bound. CTL can also be selectively separated using a flow cytometer. The cell population rich in CTL can be obtained by removing cells other than CTL from a CTL-containing culture obtained by the method for inducing CTL, the method for maintaining CTL and the method for expanding CTL of the present invention. For instance, the cell population rich in CTL can be obtained by selectively removing helper T cell using magnetic beads or a column to which an antibody against a cell surface antigen expressed on helper T cell surface, for instance, an anti-CD4 antibody, is bound, in order to remove helper T cell from the culture. Also, a flow cytometer can be used for removing helper T cell. The cell population rich in CTL thus obtained has a more potent cytotoxic activity, as compared to a cell population collected non-selectively from a CTL-containing culture, so that it is more preferably used as the CTL obtained by the method of the present invention. In addition, in the present invention, the cell population rich in CTL also encompasses a cell population of CTL alone.

In addition, CTL can be further maintained or expanded according to the method for maintaining CTL or the method for expanding CTL of the present invention using the CTL obtained by the method for maintaining CTL or the method for expanding CTL of the present invention. For instance, CTL having an even higher cytotoxic activity can also be obtained by obtaining a fraction rich in CTL according to the method described above from CTL obtained by the method for expansion of the present invention, and subjecting the fraction obtained to the method for expansion of the present invention. In addition, the cytotoxic activity of CTL obtained by the method for expansion of the present invention can be maintained by using the method for maintaining CTL of the present invention.

Further, the present invention provides CTL obtained by the method for inducing CTL, the method for maintaining CTL and the method for expanding CTL of the present invention mentioned above (including CTL collected by the above-mentioned collecting method from the CTL-containing culture obtained by these methods). All of the above-mentioned CTLs have an antigen-specific cytotoxic activity, in which there is little lowering of cytotoxic activity, even when the CTL is subjected to the continuous culture or expansion over a long period of time. In addition, the present invention provides a therapeutic agent comprising the CTL as an effective ingredient. The therapeutic agent is especially suitably used in adoptive immunotherapy. In the adoptive immunotherapy, CTL having an antigen-specific cytotoxic activity suitable for treating a patient is administered to the patient by, for instance, intravenous administration. The therapeutic agent can be prepared by, for instance, blending the CTL prepared by the method of the present invention as an effective ingredient with, for instance, a known organic or inorganic carrier suitable for parenteral administration, an excipient, a stabilizing agent and the like, according to a method known in the pharmaceutical field. As the CTL, CTL prepared by the method for expanding CTL of the present invention without using EBV-infected cell is especially preferable for this purpose. Incidentally, various conditions for the therapeutic agent, such as the content of CTL in the therapeutic agent and the dosage of the therapeutic agent, can be appropriately determined according to the known adoptive immunotherapy.

The present invention will be more concretely described by means of the examples, without by no means limiting the scope of the present invention thereto.

EXAMPLE 1

Method of Expanding CTLs Having Specific Cytotoxic Activity Using Hyaluronic Acid Example 1-1

(1) Isolation and Storage of PBMCs

Blood component was collected from a human normal individual donor having HLA-A2.1. The collected blood component was diluted 2-folds with PBS(−), overlaid on Ficoll-paque (manufactured by Pharmacia), and centrifuged at 500×g for 20 minutes. After the centrifugation, the peripheral blood mononuclear cells (PBMCs) in the intermediate layer were collected with a pipette, and washed. The collected PBMCs were suspended in a storage solution of 90% FBS (manufactured by Bio Whittaker)/10% DMSO (manufactured by SIGMA), and stored in liquid nitrogen. During CTL induction, these stored PBMCs were rapidly melted in water bath at 37° C., and washed with RPMI 1640 medium (manufactured by Bio Whittaker) containing 10 μg/ml Dnase (manufactured by Calbiochem). Thereafter, the number of living cells was calculated by trypan blue staining method, and the cells were subjected to each experiment.

(2) Induction of Anti-Influenza Virus Memory CTLs

The induction of anti-influenza virus memory CTLs was performed by partially modifying the method of Bednarek et al. [Bednarek, M. A. et al, *J. Immunology*, 147, 4047-4053 (1991)]. Concretely, PBMCs prepared in item (1) of Example 1-1 were suspended in RPMI 1640 medium (manufactured by Bio Whittaker) containing 5% human AB-type serum, 0.1 mM nonessential amino acids, 1 mM sodium pyruvate, 2 mM L-glutamine (hereinabove being all manufactured by Bio Whittaker), 10 mM HEPES (manufactured by nakalai tesque), 1% streptomycin-penicillin (manufactured by Gibco BRL) (hereinafter simply referred to as "5HRPMI") so as to have a concentration of 1 to $4 \times 10^6$ cells/ml. Thereafter, the suspension was spread on a 24-well cell culture plate (manufactured by Falcon) in a volume of 1 ml/well, and the cells were incubated in a 5% $CO_2$ wet-type incubator at 37° C. for 1.5 hours, to give plastic-adherent mononuclear cells. Thereafter, nonadherent cells were collected using RPMI 1640 medium, and stored on ice as responder cells. To separated mononuclear cells was added 0.5 ml each of 5HRPMI containing as an antigen peptide 5 μg/ml epitope peptide derived from influenza virus protein [HLA A2.1-binding peptide derived from the matrix protein of SEQ ID NO: 18 of Sequence Listing] and 1 μg/ml β2 microglobulin (manufactured by Scrips). The mixture was incubated at room temperature for 2 hours, and thereafter the cells were subjected to X-ray irradiation (5500R) to give antigen-presenting cells. The peptide solution was removed by aspiration from each of the wells, and the wells were washed with RPMI 1640 medium. Thereafter, the responder cells previously stored on ice were suspended in 5HRPMI so as to have a concentration of 0.5 to $2 \times 10^6$ cells/ml, and the suspension was added to antigen-presenting cells in an amount of 1 ml per well. At this time, hyaluronic acid (manufactured by Calbiochem) was added so as to have a final concentration of 10 μg/ml. A group without addition of the sample was set as the control. The plate was cultured at 37° C. in the presence of 5% $CO_2$. On the second day from the initiation of the culture, 1 ml of 5HRPMI containing 60 U/ml IL-2 (manufactured by Shionogi & Co., Ltd.) and 10 μg/ml hyaluronic acid was added to each well (the control containing only IL-2). Also, on the fifth day, a half of the culture supernatant was removed, and 1 ml each of IL-2 and hyaluronic acid-containing medium (the control containing only IL-2), the same as those mentioned above, was added thereto. On the seventh day, the antigen-presenting cells were prepared in the same manner as above, and thereafter the responder cells which had been cultured for one week were suspended in 5HRPMI so as to have a concentration of 0.5 to $2\times10^6$ cells/ml. The suspension was added to the antigen-presenting cells prepared in an amount of 1 ml/well each to re-stimulate the cells. At this time, hyaluronic acid was added so as to have a final concentration of 10 μg/ml (the control being without addition). On the second day from re-stimulation, 1 ml of 5HRPMI containing 60 U/ml IL-2 and 10 μg/ml hyaluronic acid was added to each well (the control containing only IL-2). Also, on the fifth day, a half of the culture supernatant was removed, and 1 ml each of the medium having the same content as that before removal was added thereto. The culture was continued for additional two days, thereby inducing CTLs.

(3) Determination for Cytotoxic Activity of CTLs

The cytotoxic activity of CTLs prepared in item (2) of Example 1-1 on the fourteenth day after the initiation of induction was evaluated by a determination method for cytotoxic activity using Calcein-AM [R. Lichtenfels et al., *J. Immunological Methods*, 172(2), 227-239 (1994)]. HLA-A2.1-having EBV transformed B-cells (name of cells: 221A2.1), which were cultured overnight together with an epitope peptide or in the absence of the epitope peptide, were suspended in RPMI 1640 medium containing 5% FBS (fetal bovine serum, manufactured by Bio Whittaker) so as to have a concentration of $1\times10^6$ cells/ml. Thereafter, Calcein-AM (manufactured by Dotite) was added to the suspension so as to have a final concentration of 25 μM, and the cells were cultured at 37° C. for 1 hour. The cells were washed with a medium not containing Calcein-AM, and thereafter mixed with K562 cells in an amount 20 times that of the cells, to give Calcein-labeled target cells. The K562 cells were used for excluding nonspecific cytotoxic activity by NK cells admixed in the responder cells.

The memory CTLs prepared in item (2) of Example 1-1 were stepwise diluted with 5HRPMI so as to have a concentration of from $1\times10^5$ to $9\times10^6$ cells/ml as effector cells. Thereafter, each of the dilutions was poured into each well of 96-well cell culture plate in an amount of 100 μl/well each. Thereto were added the Calcein-labeled target cells prepared to have a concentration of $1\times10^5$ cells/ml in an amount of 100 μl/well each. The plate containing the above-cell suspension was centrifuged at 400×g for 1 minute, and thereafter incubated in a wet-type $CO_2$ incubator at 37° C. for 4 hours. After 4 hours, 100 μl of the culture supernatant was collected from each well, and the amount of calcein released into the culture supernatant was determined by using fluorescence plate reader (485 nm/538 nm). The "specific cytotoxic activity (%)" was calculated by the following equation 1:

Specific Cytotoxic Activity (%)={(Found Value in Each Well−Minimum Released Amount)/(Maximum Released Amount−Minimum Released Amount)}×100    Equation 1

In the above equation, the minimum released amount is the amount of calcein released in the well containing only target cells and K562 cells, showing the amount of calcein naturally released from the target cells. In addition, the maximum released amount refers to the amount of calcein released when the cells are completely disrupted by adding 0.1% of the surfactant Triton X-100 (manufactured by nakalai tesque) to the target cells. As a result, the specific cytotoxic activity was induced immediately after the induction, but there were hardly any differences in the cytotoxic activity by the presence or absence of the addition of hyaluronic acid during the induction.

(4) Expansion of CTLs

CTLs prepared in item (1) of Example 1-1 were washed with 5HRPMI, and then made into a suspension having a concentration of $3\times10^4$ cells/ml. On the other hand, allogenic PBMCs not having HLA-A2.1 which were collected in the same manner as in item (1) of Example 1-1 were subjected to X-ray irradiation (3300R), and the cells were washed with the medium and then made into a suspension having a concentration of 2 to $5\times10^6$ cells/ml. These $3\times10^4$ cells of CTLs and 4 to $10\times10^6$ cells of allogenic PBMCs were suspended in 10 ml of 5HRPMI, and anti-CD3 antibody (manufactured by Janssen-Kyowa) was further added thereto so as to give a final concentration of 50 ng/ml. The mixture was placed into a flask of 12.5 cm² (manufactured by Falcon), and the cells were cultured in a wet-type $CO_2$ incubator at 37° C. for 14 days. During the culture, a group with addition of hyaluronic acid, which had been added during the CTL induction of item (2) of Example 1-1 (final concentration: 10 μg/ml), and a group without addition of hyaluronic acid were set. Stimulation by a peptide was not added at all during this expansion. On the first day after the initiation of the expansion, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. During the culture, the sample in the same concentration was added to the medium for the group with addition of hyaluronic acid. On the fourteenth day after the initiation of the expansion, the specific cytotoxic activity of CTLs was determined in the same manner as in item (3) of Example 1-1. The determination results are shown in Table 1. In the table, an E/T ratio means a ratio of the number of the effector cells (E) to the number of the target cells (T), and the peptide pulse means the presence or absence of peptide pulse to the target cells. In addition, the expansion fold was obtained as a proliferation percentage of a ratio of the cell number at the time of the termination of the expansion to the cell number at the beginning of the expansion.

TABLE 1

| | Addition of Sample* | | | | Cytotoxic Activity (%) | | | |
| | During CTL Induction | During Expansion | Expansion Fold (Times) | Peptide Pulse¶ | E/T Ratio | | | |
| Sample | | | | | 1 | 3 | 10 | 30 |
| Control | − | − | 547 | − | 7.3 | 8.4 | 9.1 | 12.7 |
| | − | − | 547 | + | 8.1 | 11.2 | 21.5 | 45.9 |
| Hyaluronic Acid | + | + | 493 | − | 7.3 | 8.6 | 13.1 | 17.0 |
| | + | + | 493 | + | 31.1 | 49.8 | 90.8 | 105.6 |

*+: sample being pulsed; −: sample not being pulsed.
¶+: peptide being pulsed; −: peptide not being pulsed.

As a result, in the groups with addition of hyaluronic acid in both of the stage during the CTL induction and the stage during the expansion, CTLs had specific, high cytotoxic activities even after the expansion for 14 days. On the other hand, in the group without addition of the sample in both of the stage during the CTL induction and the stage during the expansion, its activity was clearly lowered. In other words, it was clarified that the expansion of CTLs can be carried out with maintaining a specific, high cytotoxic activity for a long period of time by adding hyaluronic acid in the stage during the CTL induction and the stage during the expansion.

Example 1-2

(1) Induction of Anti-Influenza Virus Memory CTLs

The induction of anti-influenza virus memory CTLs was carried out in the same manner as in item (2) of Example 1-1 using the PBMCs which were isolated and stored in the same manner as in item (1) of Example 1-1. During the induction, hyaluronic acid was added to a medium so as to have a final concentration of 10 μg/ml. Further, the group without addition of the sample was set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 1-2 were expanded in the same manner as in item (4) of Example 1-1. During the expansion, hyaluronic acid which had been added during the CTL induction in item (1) of Example 1-2 was not added at all. During the expansion, stimulation by a peptide was not added at all. On the first day of the initiation of the expansion, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1. The determination results are shown in Table 2.

samples in either of the stage during the CTL induction or the stage during the expansion, its activity was clearly lowered. In other words, it was clarified that the expansion of CTLs can be carried out with maintaining the specific, high cytotoxic activity for a long period of time even if hyaluronic acid is added only during the CTL induction.

Example 1-3

(1) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1. During the induction, there were set a group with addition of hyaluronic acid (simply referred to as "HA" in Table 3) (final concentration: 10 μg/ml), and a group without addition of the sample at all. As to the groups added with hyaluronic acid, there were set a group added simultaneously together with an anti-CD44 antibody (hyaluronic acid-bound Blocking antibody; in the table referred to as "HA Blocking Anti-CD44 Antibody") or with an anti-CD44 antibody (hyaluronic acid-bound Non-blocking antibody; in the table referred to as "HA Non-blocking Anti-CD44 Antibody") each at a final concentration of 0.2 μg/ml (each being manufactured by Ancell, monoclonal antibody), and the inhibitory effects by these antibodies were studied.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 1-3 were expanded in the same manner as in item (4) of Example 1-1. During the expansion, there were set a group with addition of hyaluronic acid, which had been added during the CTL induction in item (1) of Example 1-3, so as to have a final concentration of 10 μg/ml and a group without addition of hyaluronic acid at all from the stage of induction. In addition, as to the group with addition of hyaluronic acid together with the anti-CD44 antibody, the same sample and antibody were also added during the expansion. Stimulation by a peptide was not added at all

TABLE 2

| | Addition of Sample* | | Expansion Fold (Times) | Peptide Pulse¶ | Cytotoxic Activity (%) E/T Ratio | | | |
|---|---|---|---|---|---|---|---|---|
| Sample | During CTL Induction | During Expansion | | | 1 | 3 | 10 | 30 |
| Control | − | − | 480 | − | 0 | 0 | 0.4 | 6.8 |
| | − | − | 480 | + | 4 | 11.2 | 29.3 | 59.7 |
| Hyaluronic Acid | + | + | 423 | − | 0 | 0 | 1.9 | 14.3 |
| | + | + | 423 | + | 7.2 | 23.3 | 59.6 | 85.1 |
| | + | − | 393 | − | 3.0 | 1.4 | 4.7 | 9.3 |
| | + | − | 393 | + | 9.9 | 22.1 | 47.7 | 78.0 |

*+: sample being pulsed; −: sample not being pulsed.
¶+: peptide being pulsed; −: peptide not being pulsed.

As a result, in the group with addition of hyaluronic acid only during the CTL induction, CTLs maintained specific, high cytotoxic activity even after the expansion for 14 days even when these samples were not added during the expansion. On the other hand, in the group without addition of these during the expansion. On the first day of the initiation of the expansion, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1. The determination results are shown in Table 3.

TABLE 3

| Sample | Addition of Sample* | | Expansion Fold (Times) | Peptide Pulse¶ | Cytotoxic Activity (%) E/T Ratio | | | |
|---|---|---|---|---|---|---|---|---|
| | During CTL Induction | During Expansion | | | 1 | 3 | 10 | 30 |
| Control | − | − | 330 | − | 2.4 | 6.2 | 7.4 | 9.6 |
| | − | − | 330 | + | 3.9 | 5.8 | 7.2 | 10.9 |
| HA | + | + | 350 | − | 0 | 0 | 1.9 | 5.3 |
| | + | + | 350 | + | 4.8 | 15.3 | 35.3 | 70.2 |
| HA + HA Blocking Anti-CD44 Antibody | + | + | 357 | − | 5.9 | 4.7 | 15.0 | 14.9 |
| | + | + | 357 | + | 10.9 | 11.8 | 19.5 | 17.5 |
| HA + HA Non Blocking Anti-CD44 Antibody | + | + | 413 | − | 6 | 4.7 | 5 | 7.6 |
| | + | + | 413 | + | 12.2 | 17.5 | 34.9 | 69.9 |

*+: sample being pulsed; −: sample not being pulsed.
¶+: peptide being pulsed; −: peptide not being pulsed.

As a result, in the group with addition of hyaluronic acid during the CTL induction and during the expansion, CTLs maintained specific, high cytotoxic activity even after the expansion for 14 days. On the other hand, in the group without addition of the sample in either of the stage during the CTL induction or the stage during the expansion, its activity was clearly lowered. In addition, in the group with addition of hyaluronic acid together with the anti-CD44 antibody (hyaluronic acid-bound Blocking antibody), the effect of maintaining CTL activity by hyaluronic acid was completely inhibited. On the other hand, in the group with addition of hyaluronic acid together with the anti-CD44 antibody (hyaluronic acid-bound Non-Blocking antibody), the effect of maintaining CTL activity by hyaluronic acid was not inhibited. In other words, it was clarified that the effect of maintaining cytotoxic activity by hyaluronic acid is exhibited by binding of hyaluronic acid to a CD44 antigen on the cell surface.

EXAMPLE 2

Method of Expanding CTLs Having Specific Cytotoxic Activity Using Anti-Human CD44 Antibody (1) Induction of Anti-Influenza Virus Memory CTLs The induction of anti-influenza virus memory CTLs was performed in accordance with the method described in item (2) of Example 1-1 using the PBMCs isolated and stored in accordance with the method described in item (1) of Example 1-1. During the induction, there were added a purified mouse IgG1 (manufactured by Genzyme/Techne) or the two kinds of anti-human CD44 antibodies used in item (1) of Example 1-3, each so as to have a final concentration of 0.2 µg/ml. Further, a group without addition of any antibodies was set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 2 were expanded in the same manner as in item (4) of Example 1-1. During the expansion, there were set a group with addition of mouse IgG1, which had been added during the CTL induction in item (1) of Example 2, or the above-mentioned two kinds of anti-human CD44 antibodies, each so as to have a final concentration of 0.2 µg/ml, and a group without addition of the antibody at all from the stage of induction. Stimulation by a peptide was not added at all during the expansion. On the first day of the initiation of the expansion, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 0.2 µg/ml mouse IgG1 or the above-mentioned two kinds of anti-human CD44 antibodies to each flask were carried out every 2 to 3 days. Here, in the group without addition of the antibody, the antibody was not added even during the medium exchange. On the fourteenth day after the initiation of the expansion, the specific cytotoxic activity of CTLs was determined in the same manner as in item (3) of Example 1-1. The determination results are shown in Table 4.

TABLE 4

| Sample | Addition of Sample* | | Expansion Fold (Times) | Peptide Pulse¶ | Cytotoxic Activity (%) E/T Ratio | | |
|---|---|---|---|---|---|---|---|
| | During CTL Induction | During Expansion | | | 3 | 10 | 30 |
| Control | − | − | 413 | − | 5.9 | 10.5 | 12.8 |
| | − | − | 413 | + | 4.0 | 14.8 | 48.9 |
| Mouse IgG1 | + | + | 357 | − | 5.6 | 0 | 2 |
| | + | + | 357 | + | 6.2 | 6.8 | 13.3 |

TABLE 4-continued

| Sample | Addition of Sample* | | Expansion Fold (Times) | Peptide Pulse¶ | Cytotoxic Activity (%) E/T Ratio | | |
|---|---|---|---|---|---|---|---|
| | During CTL Induction | During Expansion | | | 3 | 10 | 30 |
| HA Non Blocking | + | + | 357 | − | 10.3 | 14.2 | 21.2 |
| Anti-CD44 Antibody | + | + | 357 | + | 32.4 | 60.1 | 104.8 |
| HA Blocking | + | + | 420 | − | 1.6 | 1.3 | 3.5 |
| Anti-CD44 Antibody | + | + | 420 | + | 9.5 | 9.8 | 17.7 |

*+: sample being pulsed; −: sample not being pulsed.
¶+: peptide being pulsed; −: peptide not being pulsed.

As a result, in the group with addition of the anti-human CD44 antibody (hyaluronic acid-bound Non-Blocking antibody) during the CTL induction and during the expansion, CTLs maintained specific, high cytotoxic activity even after the expansion for 14 days. On the other hand, in the group without addition of these antibodies and the group with the anti-human CD44 antibody (hyaluronic acid-bound Blocking antibody) in both of the stage during the CTL induction and the stage during the expansion, its activity was clearly lowered. In other words, it was clarified that the expansion of CTLs can be carried out in a state in which the specific, high cytotoxic activity is maintained for a long period of time by adding an antibody not inhibiting the binding of hyaluronic acid among the anti-human CD44 antibody in the stage of CTL induction and expansion.

EXAMPLE 3

Binding Property of Hyaluronic Acid and Anti-Human CD44 Antibody with CD44 Antigen Being Soluble or Existing on Cell Surface There are two kinds of existing modes for CD44: one existing in the culture supernatant in a soluble state (hereinafter referred to as "soluble CD44") and the other existing on the surface of cell membrane (hereinafter referred to as "CD44 existing on cell surface"). CD44 is a receptor of hyaluronic acid, and hyaluronic acid has an effect of maintaining cytotoxic activity by its addition during the expansion. Therefore, which of the CD44 antigens the effect of maintaining the activity is dependent upon was studied.

Example 3-1

(1) Evaluation of Binding Property of Soluble CD44 and Hyaluronic Acid

The binding property of the soluble CD44 and hyaluronic acid was evaluated by the following method. Concretely, Nunc-Immuno plate (manufactured by Nunc), to which PBS (manufactured by Nissui) containing 5 µg/ml anti-human CD44 antibody (soluble CD44-recognizing antibody, manufactured by Ancell) had been poured into each well at 100 µl/well and the plate which was preincubated at room temperature overnight, was washed with 0.025% Tween 20 (manufactured by SIGMA)/PBS three times. Thereafter, Blockace (manufactured by Dainippon Pharmaceutical Co., Ltd.) was added thereto at 300 µl/well, and the incubation was carried out at room temperature for 1 hour or more. On the other hand, hyaluronic acid was added to a soluble CD44 (15 ng/ml)-containing RPMI medium so as to have a final concentration of 0, 0.25, 0.5 or 1 µg/ml, and the media were preincubated at 37° C. for 1 hour. Each well of the plate after blocking was washed again three times with 0.025% Tween 20/PBS, and each of preincubated soluble CD44 (15 ng/ml)-containing RPMI medium with or without hyaluronic acid was added at 100 µl/well. Further, an HRP-labeled conjugate (reagent attached to ELISA system for determining soluble CD44, manufactured by BenderMed) was added to each well at 50 µl/well, and the incubation was carried out at room temperature for 3 hours. After the incubation, each well was washed three times with 0.025% Tween 20/PBS, a TMB (3,3',5,5'-tetramethylbenzidine) solution (manufactured by SIGMA) was added at 100 µl/well, the incubation was carried out at room temperature for 15 minutes, and 2 N sulfuric acid was added thereto at 50 µl/well to stop the reaction. Each absorbance was determined using a plate reader (450 nm). The determination results are shown in FIG. 1.

As a result, even when hyaluronic acid was added to the soluble CD44-containing medium, the recognition by the soluble CD44-recognizing antibody was not inhibited at all. In other words, hyaluronic acid did not bind to the soluble CD44 existing in the medium at all. It was clarified from this finding that the soluble CD44 in the medium is not involved at all in the effect of maintaining the specific cytotoxic activity of CTLs by hyaluronic acid.

(2) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1.

The cytotoxic activity of CTLs prepared as described above on the fourteenth day after the initiation of induction was evaluated in the same manner as in item (3) of Example 1-1. As a result, the specific cytotoxic activity was induced immediately after the induction.

(3) Expansion of CTLs

CTLs prepared in item (2) of Example 3-1 were expanded in the same manner as in item (4) of Example 1-1. Stimulation by a peptide was not added at all during this expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1. It was confirmed that these CTLs have specific cytotoxic activity.

(4) Evaluation of Binding Property of Hyaluronic Acid and CD44 on Cell Surface

Figure 2:
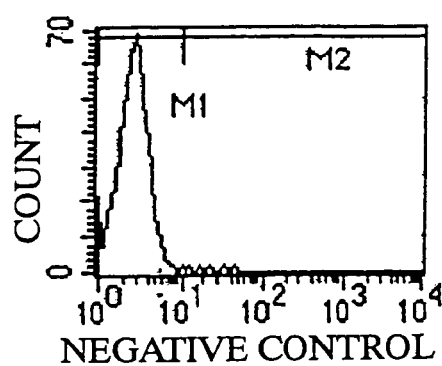
FIG. 2 is a graph showing a binding activity of FL-labeled hyaluronic acid and CD44 on CTL cell surface.
Figure 2:
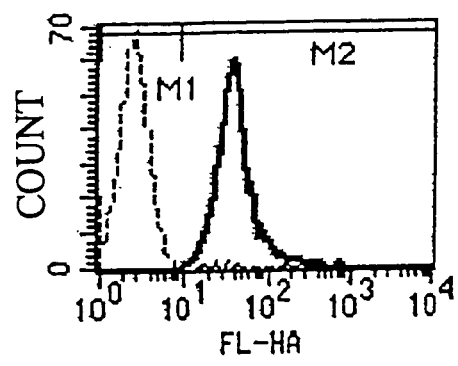

The CTLs prepared in item (3) of Example 3-1 in an amount of $2 \times 10^5$ cells were immobilized with PBS (manufactured by Nissui) containing 1% paraformaldehyde (manufactured by nakalai tesque), and washed with PBS. The immobilized cells were suspended in PBS containing 10 µg/ml FL-labeled hyaluronic acid (manufactured by Molecular Probes), and the cells were incubated at 37° C. for 30 minutes. As a negative control, a group to be incubated in PBS without containing FL-labeled hyaluronic acid (FL-HA) was also set. After the incubation, the cells were washed with PBS, and suspended again in PBS containing 1% paraformaldehyde. The prepared CTLs were applied to FACS Vantage (manufactured by Becton, Dickinson) to determine fluorescent intensity on the cell surface of CTLs. The results are shown in FIG. 2.

As a result, the FL-labeled hyaluronic acid was bound to the cell surface of CTLs. In other words, it was clarified that the effect of maintaining the specific cytotoxic activity of CTLs by hyaluronic acid is exhibited by the binding of hyaluronic acid to CD44 existing on the cell surface of CTLs.

Example 3-2

(1) Evaluation of Binding Property of Anti-Human CD44 Antibody (HA Non-Blocking Anti-CD44 Antibody) and Soluble CD44

Figure 3:
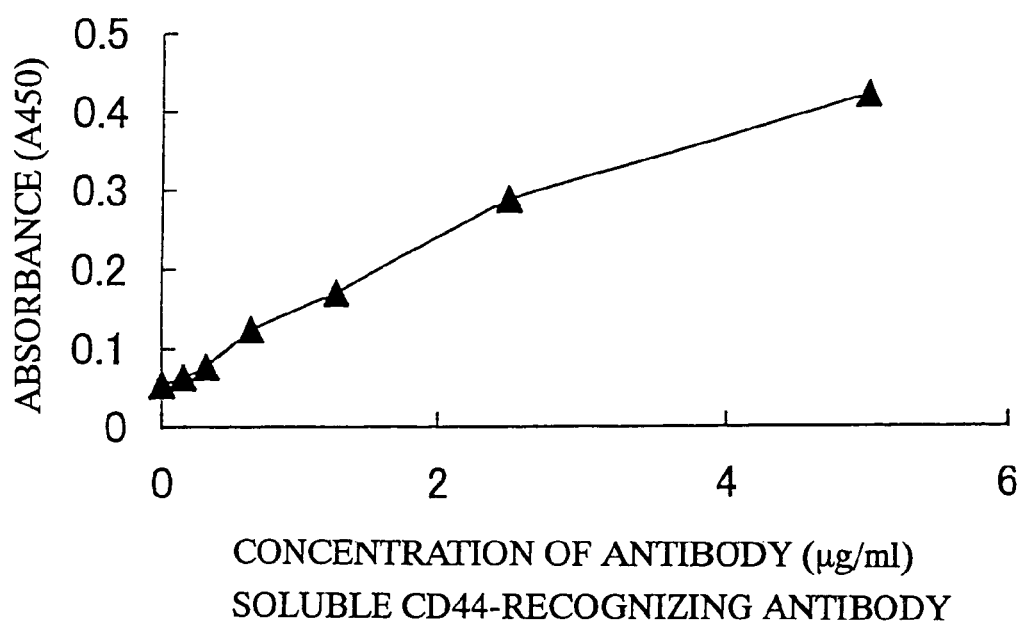
FIG. 3 is a graph showing a binding activity of a soluble CD44-recognizing antibody and a soluble CD44 in a medium.
Figure 4:
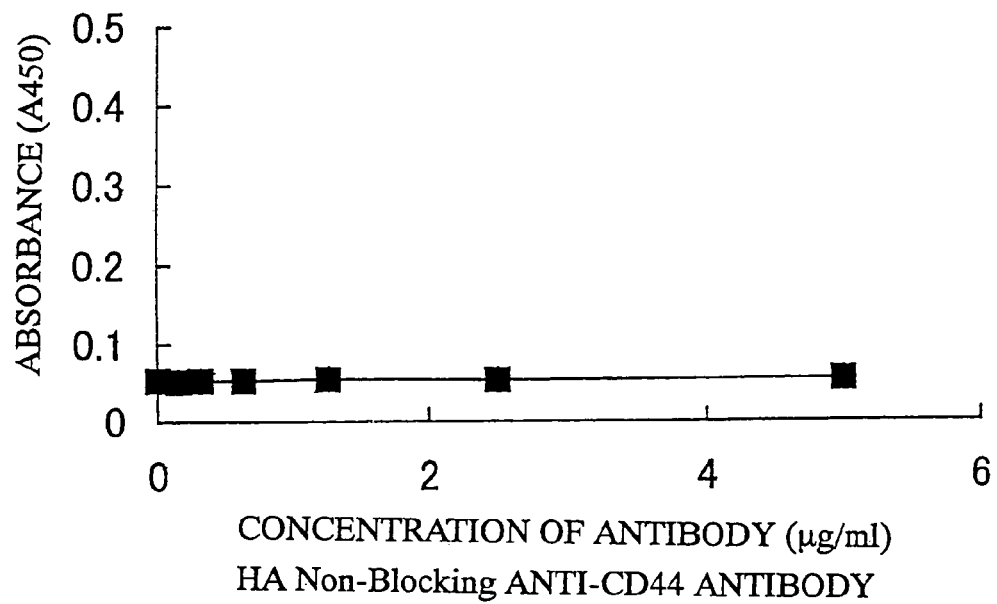
FIG. 4 is a graph showing a binding activity of an HA Non-Blocking anti-CD44 antibody and a soluble CD44 in a medium.

The binding property of the HA Non-Blocking anti-CD44 antibody and the soluble CD44 was evaluated by the following method. Concretely, the Nunc-Immuno plate (manufactured by Nunc) to which PBS (manufactured by Nissui) containing 5 µg/ml of HA Non-Blocking anti-CD44 antibody or anti-human CD44 antibody (soluble CD44-recognizing antibody) (manufactured by Ancell) as a primary antibody had been poured at 100 µl/well, and the plate which was incubated at room temperature overnight, was washed three times with 0.025% Tween 20 (manufactured by SIGMA)/PBS. Thereafter, Blockace (manufactured by Dainippon Pharmaceutical) was added thereto at 300 µl/well, and the incubation was carried out at room temperature for 1 hour or more. Each well of the plate after blocking was washed again three times with 0.025% Tween 20/PBS, and the soluble CD44 (15 ng/ml)-containing RPMI medium was added thereto at 100 µl/well. Further, an HRP-labeled conjugate (reagent attached to ELISA system for measuring soluble CD44, manufactured by BenderMed) was added to each well at 50 µl/well, and the incubation was carried out at room temperature for 3 hours. After incubation, each well was washed three times with 0.025% Tween 20/PBS, TMB solution (manufactured by SIGMA) was added thereto at 100 µl/well, the incubation was carried out at room temperature for 15 minutes, and thereafter 2 N sulfuric acid was added thereto at 50 µl/well to stop the reaction. Each absorbance was determined with a plate reader (450 nm). Experiments were carried out twice, and an average value was taken. The results are shown in FIGS. 3 and 4. As a result, the soluble CD44-recognizing antibody used as a primary antibody recognized the soluble CD44 in the medium in an antibody concentration-dependent manner. On the other hand, the HA Non-Blocking anti-CD44 antibody did not recognize the soluble CD44 in the medium at all. In other words, the HA Non-Blocking anti-CD44 antibody did not bind to the soluble CD44 existing in the medium. It was clarified from this finding that the soluble CD44 in the medium is not involved at all in the effect of maintaining the specific cytotoxic activity of CTLs by the HA Non-Blocking anti-CD44 antibody.

(2) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1.

The cytotoxic activity of CTLs prepared as described above on the fourteenth day after the initiation of induction was evaluated in the same manner as in item (3) of Example 1-1. As a result, the specific cytotoxic activity was induced immediately after the induction.

(3) Expansion of CTLs

CTLs prepared in item (2) of Example 3-2 were expanded in the same manner as in item (4) of Example 1-1. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1, and it was confirmed that these CTLs have specific cytotoxic activity.

Figure 5:
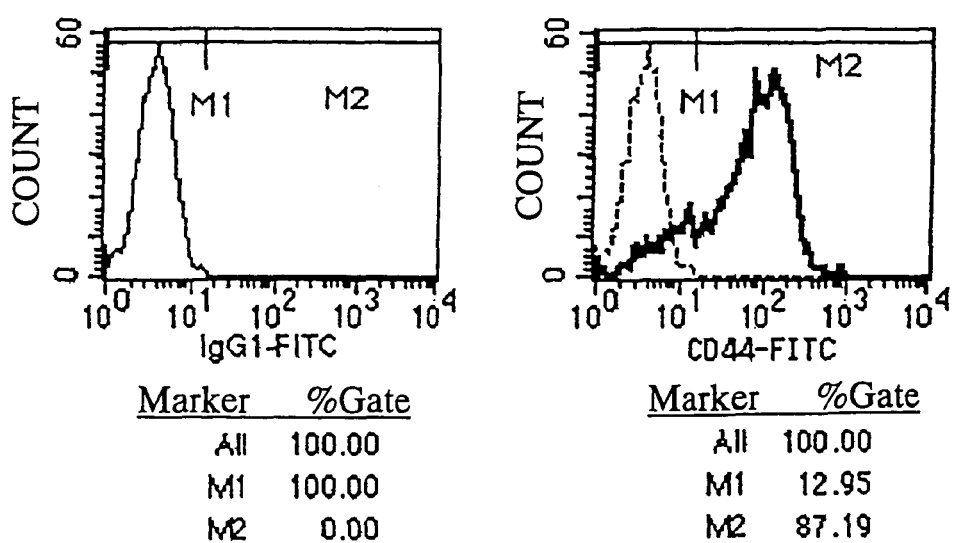
FIG. 5 is a graph showing a binding activity of an HA Non-Blocking anti-CD44 antibody and CD44 on CTL cell surface.

(4) Evaluation of Binding Property of Anti-Human CD44 Antibody (HA Non-Blocking Anti-CD44 Antibody) and CD44 on Cell Surface The CTLs prepared in item (3) of Example 3-2 in an amount of $2 \times 10^5$ cells were immobilized with PBS (manufactured by Nissui) containing 1% paraformaldehyde (manufactured by nakalai tesque), and thereafter washed with PBS. The immobilized cells were suspended in PBS containing 1% BSA (manufactured by SIGMA) and 1 µg/ml anti-CD44/FITC (FITC-labeled HA Non-Blocking anti-CD44 antibody (CD44-FITC), manufactured by Ancell), and the cells were incubated on ice for 30 minutes. As a control, a group to be incubated in PBS containing 1 µg/ml mouse IgG1/FITC (FITC-labeled mouse IgG antibody (IgG1-FITC), manufactured by DAKO) was also set. After the incubation, the cells were washed with PBS, and suspended again in PBS containing 1% paraformaldehyde. The prepared CTLs were applied to FACS Vantage to determine the fluorescent intensity on the cell surface of CTLs. The results are shown in FIG. 5.

As a result, the FITC-labeled HA-Non-Blocking anti-CD44 antibody was bound to the cell surface of CTLs. In other words, there was suggested a possibility that the effect of maintaining the specific cytotoxic activity of CTLs by the anti-human HA Non-Blocking anti-CD44 antibody is exhibited by binding of hyaluronic acid to CD44 existing on the cell surface of CTLs.

Example 3-3

(1) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1. During the induction, the HA Non-Blocking Anti-CD44 antibody was added so as to have a final concentration of 0.2 µg/ml. Further, a group without addition of the antibody was also set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 3-3 were expanded in the same manner as in item (4) of Example 1-1. During the expansion, the HA Non-Blocking Anti-CD44 antibody, which had been added during the induction of CTLs in item (1) of Example 3-3, was each added so as to have a final concentration of 0.2 µg/ml. In addition, as to the group without addition of the antibody during the induction, the antibody was not added at this stage. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 0.2 µg/ml HA Non-Blocking Anti-CD44 antibody to each flask were carried out every 2 to 3 days. Here, in the group without addition of the antibody, the antibody was not added even during the medium exchange. On the fourteenth day after the initiation of the expansion, the specific cytotoxic activity of CTLs was determined in the same manner as in item (3) of Example 1-1. As a result, it was confirmed that in the group with addition of HA Non-Blocking Anti-CD44 antibody during the induction of CTLs and during the expansion, the CTLs maintained a specific, high cytotoxic activity even after the expansion for fourteen days. On the other hand, it was confirmed that in the group without addition of these antibodies during neither the induction of CTLs nor the expansion, its activity was clearly lowered.

Figure 6:
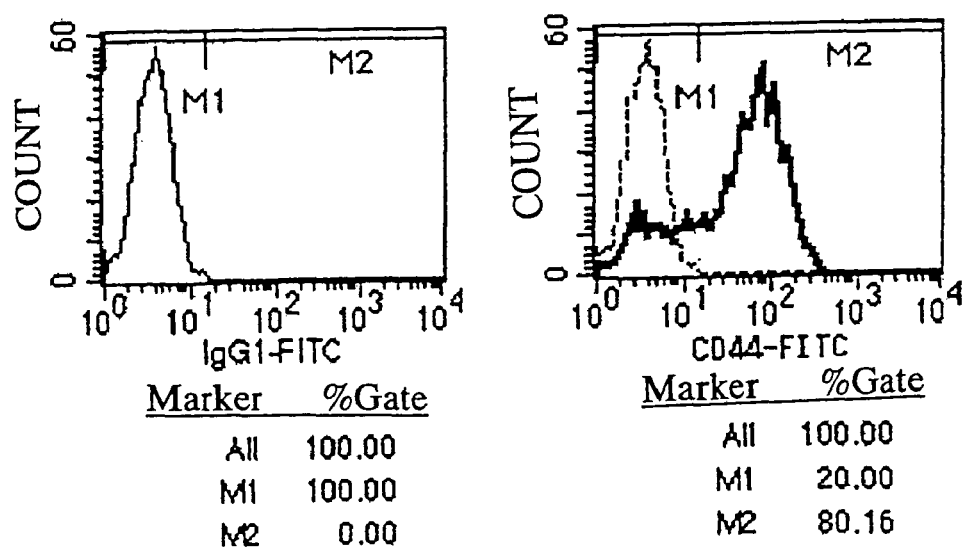
FIG. 6 is a graph showing a binding of an HA Non-Blocking anti-CD44 antibody on cell surface of CTL after expansion of CTL in which the antibody is added to a medium.

(3) Evaluation of Binding Property of Antibody on Cell Surface of CTLs After Expansion with Addition of HA Non-Blocking Anti-CD44 Antibody The CTLs prepared in item (1) of Example 3-3 in an amount of $2 \times 10^5$ cells (CTLs cultured under the conditions of addition of HA Non-Blocking Anti-CD44 Antibody) were immobilized with PBS (manufactured by Nissui) containing 1% paraformaldehyde (manufactured by nakalai tesque), and washed with PBS. The immobilized cells were suspended in PBS containing 1% BSA (manufactured by SIGMA) and 1 µg/ml FITC-labeled mouse IgG or FITC-labeled anti-mouse IgG antibody, and the cells were incubated on ice for 30 minutes. After the incubation, the cells were washed with PBS, and suspended again in PBS containing 1% paraformaldehyde. The prepared CTLs were analyzed by FACS Vantage to determine the fluorescent intensity on the cell surface of CTLs. The results are shown in FIG. 6.

As a result, binding of the HA Non-Blocking anti-CD44 antibody was confirmed on the cell surface of CTLs obtained by expanding under the conditions of addition of this antibody. In other words, it was clarified that the effect of maintaining the specific cytotoxic activity of CTLs by the HA Non-Blocking anti-CD44 antibody is exhibited by binding of this antibody to CD44 existing on the cell surface of CTLs.

EXAMPLE 4

Expansion of CTLs Maintaining Specific Cytotoxic Activity Using Anti-Human HGF Antibody Example 4-1

(1) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1. During the induction, a purified mouse IgG1 (manufactured by Genzyme/Techne) or an anti-human HGF antibody (mouse monoclonal antibody; manufactured by Genzyme/Techne) was added so as to have a final concentration of 2 µg/ml. Further, a group without addition of antibody was also set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 4-1 were expanded in the same manner as in item (4) of Example 1-1. During the expansion, there were set a group with addition of the mouse IgG1 or the anti-human HGF antibody, which had been added during the induction of CTLs in item (1) of Example 4-1, each so as to have a final concentration of 2 µg/ml, and a group without addition of the antibody at all from the stage of the induction. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 2 µg/ml mouse IgG1 or anti-human HGF antibody to each flask were carried out every 2 to 3 days. Here, in the group without addition of the antibody, the antibody was not added even during the medium exchange. On the fourteenth day after the initiation of the expansion, the specific cytotoxic activity of CTLs was determined in the same manner as in item (3) of Example 1-1. The determination results are shown in Table 5.

TABLE 5

| | Addition of Sample* | | | | Cytotoxic Activity (%) | | | |
| | During CTL Induction | During Expansion | Expansion Fold (Times) | Peptide Pulse¶ | E/T Ratio | | | |
| Sample | | | | | 1 | 3 | 10 | 30 |
|---|---|---|---|---|---|---|---|---|
| Control | − | − | 340 | − | 0.6 | 0.6 | 1.5 | 19.4 |
| | − | − | 340 | + | 0 | 3.2 | 6.8 | 21.3 |
| Mouse IgG1 | + | + | 207 | − | 0 | 0 | 0.1 | 3.9 |
| | + | + | 207 | + | 0 | 4.1 | 9.3 | 30.3 |
| Anti-HGF Antibody | + | + | 435 | − | 1.2 | 3.1 | 0 | 4.0 |
| | + | + | 435 | + | 7.2 | 19.5 | 39.6 | 74.5 |

*+: sample being pulsed; −: sample not being pulsed.
¶+: peptide being pulsed; −: peptide not being pulsed.

As a result, in the group with addition of the anti-human HGF antibody during the induction of CTLs and during the expansion, the CTLs maintained a specific, high cytotoxic activity even after the expansion for fourteen days. On the other hand, in the group without addition of these antibodies during neither the induction of CTLs nor the expansion, its activity was clearly lowered. In other words, it was clarified that the expansion of CTLs can be carried out in a state in which a specific, high cytotoxic activity is maintained for a long period of time by adding the anti-human HGF antibody during the induction of CTLs and during the expansion.

Example 4-2

(1) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1. During the induction, an anti-human HGF antibody (mouse monoclonal antibody; manufactured by Genzyme/Techne) was added so as to have a final concentration of 2 µg/ml. Further, a group without addition of antibody was also set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 4-2 were expanded in the same manner as in item (4) of Example 1-1. During the expansion, the anti-human HGF antibody, which had been added during the induction of CTLs in item (1) of Example 4-2, was not added at all. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1. The determination results are shown in Table 6.

As a result, in the group with addition of the anti-human HGF antibody only during the induction of CTLs, a specific, high cytotoxic activity was maintained after the expansion for fourteen days even when the antibody was not added during the expansion. On the other hand, in the group without addition of the antibody during neither the induction of CTLs nor the expansion, its activity was clearly lowered. In other words, it was clarified that the expansion of CTLs can be carried out in a state in which a specific, high cytotoxic activity is maintained for a long period of time even when the anti-human HGF antibody was added only during the induction of CTLs.

EXAMPLE 5

Expansion of CTLs Maintaining Specific Cytotoxic Activity Using Anti-Human IGF-1 Antibody Example 5-1

(1) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1. During the induction, a purified goat IgG (manufactured by CHEMICON International) or an anti-human IGF-1 antibody (goat polyclonal antibody; manufactured by Genzyme/Techne) was added so as to have a final concentration of 2 µg/ml. Further, a group without addition of antibody was also set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 5-1 were expanded in the same manner as in item (4) of Example 1-1. During the expansion, there were set a group with addition of the goat IgG or anti-human IGF-1 antibody, which had been added during the induction of CTLs in item (1) of Example 5-1 each so as to have a final concentration of 2 µg/ml, and a group without addition of the antibody at all from the stage of the induction. Stimulation by a peptide was not added at all

TABLE 6

| Sample | Addition of Sample* During CTL Induction | During Expansion | Expansion Fold (Times) | Peptide Pulse¶ | Cytotoxic Activity (%) E/T Ratio | | | |
|---|---|---|---|---|---|---|---|---|
| | | | | | 1 | 3 | 10 | 30 |
| Control | − | − | 547 | − | 7.3 | 8.4 | 9.1 | 12.7 |
| | − | − | 547 | + | 8.1 | 11.2 | 21.5 | 45.9 |
| Anti-HGF Antibody | + | + | 540 | − | 6.8 | 7.3 | 8.5 | 10.2 |
| | + | + | 540 | + | 23.3 | 40.8 | 72.4 | 103.4 |
| | + | − | 463 | − | 7.4 | 7.9 | 10.5 | 14.4 |
| | + | − | 463 | + | 22.2 | 38.1 | 70.4 | 94.5 |

*+: sample being pulsed; −: sample not being pulsed.

¶+: peptide being pulsed; −: peptide not being pulsed.

during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 2 µg/ml goat IgG or anti-human IGF-1 antibody to each flask were carried out every 2 to 3 days. Here, in the group without addition of the antibody, the antibody was not added even during the medium exchange. On the fourteenth day after the initiation of the expansion, the specific cytotoxic activity of CTLs was determined in the same manner as in item (3) of Example 1-1. The determination results are shown in Table 7.

TABLE 7

| Sample | Addition of Sample* | | Expansion Fold (Times) | Peptide Pulse¶ | Cytotoxic Activity (%) E/T Ratio | | | |
|---|---|---|---|---|---|---|---|---|
| | During CTL Induction | During Expansion | | | 1 | 3 | 10 | 30 |
| Control | − | − | 340 | − | 0.8 | 0.6 | 1.5 | 19.4 |
| | − | − | 340 | + | 0 | 3.2 | 6.8 | 21.3 |
| Goat IgG | + | + | 463 | − | 0 | 0 | 1.6 | 5.6 |
| | + | + | 463 | + | 0.7 | 2.1 | 6.6 | 18.9 |
| Anti-IGF-1 Antibody | + | + | 368 | − | 0 | 0 | 0.4 | 3.4 |
| | + | + | 368 | + | 13.0 | 40.2 | 80.4 | 90.9 |

*+: sample being pulsed; −: sample not being pulsed.
¶+: peptide being pulsed; −: peptide not being pulsed.

As a result, in the group with addition of the anti-human IGF-1 antibody during the induction of CTLs and during the expansion, the CTLs maintained a specific, high cytotoxic activity even after the expansion for fourteen days. On the other hand, in the group without addition of these antibodies during neither the induction of CTLs nor the expansion, its activity was clearly lowered. In other words, it was clarified that the expansion of CTLs can be carried out in a state in which a specific, high cytotoxic activity is maintained for a long period of time by adding the anti-human IGF-1 antibody during the induction of CTLs and during the expansion.

Example 5-2

(1) Induction of Anti-Influenza Virus Memory CTLs he induction of anti-influenza virus memory CTLs was performed in accordance with the method described in item (2) of Example 1-1 using the PBMCs isolated and stored in accordance with the method described in item (1) of Example 1-1. During the induction, an anti-human IGF-1 antibody (goat polyclonal antibody; manufactured by Genzyme/Techne) was added so as to have a final concentration of 2 µg/ml. Further, a group without addition of antibody was also set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs CTLs prepared in item (1) of Example 5-2 were expanded in the same manner as in item (4) of Example 1-1. During the expansion, the anti-human IGF-1 antibody, which had been added during the induction of CTLs in item (1) of Example 5-2, was not added at all. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1. The determination results are shown in Table 8.

TABLE 8

| Sample | Addition of Sample* | | Expansion Fold (Times) | Peptide Pulse¶ | Cytotoxic Activity (%) E/T Ratio | | |
|---|---|---|---|---|---|---|---|
| | During CTL Induction | During Expansion | | | 1 | 3 | 10 |
| Control | − | − | 547 | − | 7.3 | 8.4 | 9.1 |
| | − | − | 547 | + | 8.1 | 11.2 | 21.5 |
| Anti-IGF-1 Antibody | + | + | 637 | − | 3.8 | 3.2 | 7.5 |
| | + | + | 637 | + | 20.8 | 47.4 | 69.0 |
| | + | − | 553 | − | 9.4 | 11.6 | 15.0 |
| | + | − | 553 | + | 49.6 | 82.6 | 111.0 |

*+: sample being pulsed; −: sample not being pulsed.
¶+: peptide being pulsed; −: peptide not being pulsed.

As a result, in the group with addition of the anti-human IGF-1 antibody during the induction of CTLs, a specific, high cytotoxic activity was maintained after the expansion for fourteen days even when the antibody was not added during the expansion. On the other hand, in the group without addition of the antibody during neither the induction of CTLs nor the expansion, its activity was clearly lowered. In other words, it was clarified that the expansion of CTLs can be carried out in a state in which a specific, high cytotoxic activity is maintained for a long period of time even when the anti-human IGF-1 antibody was added only during the induction of CTLs.

EXAMPLE 6

Expansion of CTLs Maintaining Specific Cytotoxic Activity Using Anti-Human IGF-2 Antibody (1) Induction of Anti-Influenza Virus Memory CTLs The induction of anti-influenza virus memory CTLs was performed in accordance with the method described in item (2) of Example 1-1 using the PBMCs isolated and stored in accordance with the method described in item (1) of Example 1-1. During the induction, a purified mouse IgG1 (manufactured by Genzyme/Techne) or an anti-human IGF-2 antibody (mouse monoclonal antibody; manufactured by Genzyme/Techne) was added so as to have a final concentration of 2 μg/ml. Further, a group without addition of antibody was also set.

The cytotoxic activity of CTLs prepared as described above on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of the addition of the antibody during the induction.

(2) Expansion of CTLs

CTLs prepared in item (1) of Example 6 were expanded in the same manner as in item (4) of Example 1-1. During the expansion, there were set a group with addition of the mouse IgG1 or anti-human IGF-2 antibody, which had been added during the induction of CTLs in item (1) of Example 6 each so as to have a final concentration of 2 μg/ml, and a group without addition of the antibody at all from the stage of the induction. Stimulation by a peptide was not added at all during the expansion. On the first day of the initiation of the culture, IL-2 was added so as to have a final concentration of 120 U/ml. Further, on the fourth day and on after the initiation of the expansion, procedures of removing a half of the culture supernatant, and thereafter adding 5 ml of 5HRPMI containing 60 U/ml IL-2 and 2 μg/ml mouse IgG1 or anti-human IGF-2 antibody to each flask were carried out every 2 to 3 days. Here, in the group without addition of the antibody, the antibody was not added even during the medium exchange. On the fourteenth day after the initiation of the expansion, the specific cytotoxic activity of CTLs was determined in the same manner as in item (3) of Example 1-1. The determination results are shown in Table 9.

TABLE 9

| Sample | Addition of Sample* | | Expansion Fold (Times) | Peptide Pulse¶ | Cytotoxic Activity (%) E/T Ratio | | | |
|---|---|---|---|---|---|---|---|---|
| | During CTL Induction | During Expansion | | | 1 | 3 | 10 | 30 |
| Control | − | − | 237 | − | 2.1 | 3.9 | 5.6 | 9.7 |
| | − | − | 237 | + | 0 | 4.1 | 6.9 | 12.4 |
| Mouse IgG1 | + | + | 370 | − | 0 | 0 | 0 | 0 |
| | + | + | 370 | + | 0 | 0 | 0 | 3.1 |
| Anti-IGF-2 Antibody | + | + | 225 | − | 3.9 | 5.0 | 5.8 | 10.2 |
| | + | + | 225 | + | 7.1 | 16.5 | 37.7 | 71.5 |

*+: sample being pulsed; −: sample not being pulsed.
¶+: peptide being pulsed; −: peptide not being pulsed.

As a result, in the group with addition of the anti-human IGF-2 antibody during the induction of CTLs and during the expansion, the CTLs maintained a specific, high cytotoxic activity even after the expansion for fourteen days. On the other hand, in the group without addition of the antibody during neither the induction of CTLs nor the expansion, its activity was clearly lowered. In other words, it was clarified that the expansion of CTLs can be carried out in a state in which a specific, high cytotoxic activity is maintained for a long period of time even when the anti-human IGF-2 antibody was added only during the induction of CTLs.

EXAMPLE 7

Expansion of CTLs Maintaining Tumor-Associated Antigen-Specific Cytotoxic Activity

Example 7-1

(1) Induction of Anti-Tumor-Associated Antigen (MAGE3)-Specific CTLs

The induction of anti-tumor-associated antigen (melanoma-associated antigen 3, MAGE3)-specific CTLs was performed using the PBMCs isolated and stored in accordance with the method described in item (1) of Example 1-1. The induction of the anti-tumor-associated antigen (MAGE3)-specific CTLs was carried out by partly modifying the method of Plebanski M. et al. [Eur. *J. Immunol.*, 25(6), 1783-1787 (1995)]. Concretely, PBMCs prepared in item (1) of Example 1-1 were suspended in 5HRPMI so as to have a concentration of 2 to 4×10$^7$ cells/ml, and thereafter the suspension was divided into halves. A half was stored as responder cells on ice, the other half was used as antigen presenting cells, and an equivolume of 5HRPMI containing 80 μg/ml melanoma antigen MAGE3-derived epitope peptide (melanoma antigen MAGE3-derived HLA-A2.1 binding peptide described in SEQ ID NO: 19 of Sequence Listing) as an antigen peptide and 6 μg/ml β2 microglobulin (manufactured by Scrips) was added thereto, and the cells were incubated at 37° C. for 2 hours in a 5% CO$_2$ wet incubator. Thereafter, the cells were washed with 5HRPMI, and the washed cells were mixed with the responder cells stored on ice, and thereafter a concentration was made to 2×10⁶ cells/ml. IL-7 and KLH were added thereto so as to have final concentrations of 25 ng/ml and 5 μg/ml, respectively, and each mixture was placed into a 24-well cell culture plate (manufactured by Falcon) at 2 ml/well. At this stage, hyaluronic acid (manufactured by Calbiochem) was added so as to have a final concentration of 10 μg/ml. In addition, as a control, a group without addition of the sample was also set. The plate was subjected to culture at 37° C. in 5% $CO_2$. On the fourth day after the initiation of the culture, a half of the culture supernatant was removed, and 1 ml of 5HRPMI containing 60 U/ml IL-2 and 10 μg/ml hyaluronic acid (the control containing only IL-2) was added to each well. On the seventh day, antigen presenting cells were prepared in the same manner as described above, and the cells were irradiated with X-ray (5500R) and prepared so as to have a concentration of 4×10⁶ cells/ml. The responder cells which had been cultured for 1 week were suspended in 5HRPMI so as to have a concentration of 2×10⁶ cells/ml, and mixed with an equivolume of the prepared antigen presenting cells, and each mixture was added to a 24-well cell culture plate at 1 ml/well, and IL-7 was further added so as to have a final concentration of 25 ng/ml to re-stimulate the cells. At this stage, hyaluronic acid was added thereto so as to have a final concentration of 10 μg/ml (in the case of the control, not being added). On the first day after re-stimulation, 1 ml of 5HRPMI containing 60 U/ml IL-2 and 10 μg/ml hyaluronic acid (the control containing only IL-2) was added to each well. On the third day, a half of the culture supernatant was removed, and the medium having the same content as that before removing the supernatant was added in an amount of 1 ml each. The same re-stimulation was carried out once a week for a total of four times, to induce CTLs.

(2) Determination for Cytotoxic Activity of CTLs

The cytotoxic activity of CTLs prepared in item (1) of Example 7-1 on the thirty-fifth day after the initiation of induction was evaluated in the same manner as in item (3) of Example 1-1. Here, as target cells, there were used HLA-A2.1-having EBV transformed B-cells (name of cells: 221A2.1), which were cultured overnight together with the epitope peptide or in the absence of the epitope peptide. As a result, the specific cytotoxic activity was induced immediately after the induction, but there were hardly any differences in the cytotoxic activity by the presence or absence of the addition of hyaluronic acid during the induction.

(3) Expansion of CTLs

CTLs prepared in item (1) of Example 7-1 were expanded in the same manner as in item (4) of Example 1-1. During the expansion, there were set a group with addition of hyaluronic acid, which had been added during the induction of CTLs in item (1) of Example 7-1, so as to have a concentration of 10 μg/ml, and a group without addition of the sample at all from the stage of the induction. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 10 μg/ml hyaluronic acid to each flask were carried out every 2 to 3 days. Here, in the group without addition of the sample, the sample was not added even during the medium exchange. On the fourteenth day after the initiation of the expansion, the specific cytotoxic activity of CTLs was determined in the same manner as in item (3) of Example 1-1. The determination results are shown in Table 10.

TABLE 10

| Sample | Addition of Sample* | | Expansion Fold (Times) | Peptide Pulse¶ | Cytotoxic Activity (%) E/T Ratio | |
| | During CTL Induction | During Expansion | | | 2 | 6 |
| --- | --- | --- | --- | --- | --- | --- |
| Control | − | − | 237 | − | 0 | 0 |
|  | − | − | 237 | + | 29.8 | 56.0 |
| Hyaluronic Acid | + | + | 217 | − | 3.6 | 0 |
|  | + | + | 217 | + | 50.3 | 67.7 |

*+: sample being pulsed; −: sample not being pulsed.
¶+: peptide being pulsed; −: peptide not being pulsed.

As a result, in the group with addition of hyaluronic acid during the CTL induction and during the expansion, the CTLs maintained a specific, high cytotoxic activity even after the expansion for 14 days. On the other hand, in the group without addition of the sample during the CTL induction and during the expansion, its activity was clearly lowered. In other words, it was clarified that the expansion of CTLs for the anti-tumor associated antigen (MAGE3) can be carried out in a state in which a specific, high cytotoxic activity was maintained for a long period of time by adding hyaluronic acid during the CTL induction and during the expansion.

Example 7-2

(1) Induction of Anti-Tumor-Associated Antigen(MART1)-Specific CTLs

The induction of anti-tumor-associated antigen(melanoma antigen recognized by T cell, MART1)-specific CTLs was carried out in the same manner as in item (1) of Example 7-1 using the PBMCs which were isolated and stored in the same manner as in item (1) of Example 1-1. As an antigen peptide, an epitope peptide derived from melanoma antigen MART1 (HLA A2. 1-binding peptide derived from melanoma antigen MART1 of SEQ ID NO: 20 of Sequence Listing). At this stage, hyaluronic acid (manufactured by Calbiochem) was added to the medium so as to have a final concentration of 10 μg/ml. Also, as the control, a group without addition of the sample was also set.

The cytotoxic activity of CTLs which were thus prepared on the thirty-fifth day after the initiation of the induction was evaluated in the same manner as in item (3) of Example 1-1. Here, in the evaluation, as target cells, there were used HLA-A2.1-having EBV transformed B-cells (name of cells: 221A2.1) which were cultured overnight together with the epitope peptide or in the absence of the epitope peptide; a cancer cell line having HLA-A2.1 (name of cells: 624mel; HLA-A2.1-having MART1-expressing cells) which was cultured for two nights in the presence of 100 U/ml IFN-γ; or a cancer cell line not having HLA-A2.1 (name of cells: 888mel; HLA-A2.1-not having MART1-expressing cells).

As a result, the specific cytotoxic activity was induced immediately after the induction, but there were hardly any differences in the cytotoxic activity by the presence or absence of the addition of the sample during the induction.

(2) Expansion of CTLs

CTLs prepared in item (1) of Example 7-2 were expanded in the same manner as in item (4) of Example 1-1. During the expansion, there were set a group with addition of hyaluronic acid, which had been added during the CTL induction in item (1) of Example 7-2, so as to have a concentration of 10 μg/ml and a group without addition of the sample at all from the stage of the induction. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 10 μg/ml hyaluronic acid to each flask were carried out every 2 to 3 days. Here, in the group without addition of the sample, the sample was not added even during medium exchange. On the fourteenth day after the initiation of the expansion, the specific cytotoxic activity of CTLs was determined in the same manner as in item (3) of Example 1-1. The determination results are shown in Table 11.

EXAMPLE 8

Comparison with REM Method and Combination with REM Method (1) Induction of Anti-Influenza Virus Memory CTLs The induction of anti-influenza virus memory CTLs was carried out in the same manner as in item (2) of Example 1-1 using the PBMCs which were isolated and stored in the same manner as in item (1) of Example 1-1. During the induction, hyaluronic acid was added to a medium so as to have a final concentration of 10 μg/ml. Further, the group without addition of the sample was also set.

The cytotoxic activity of CTLs which were thus prepared on the fourteenth day after the initiation of induction was evaluated in the same manner as in item (3) of Example 1-1. As the antigen peptide, a 5 μg/ml epitope peptide derived from influenza virus protein described in item (2) of Example 1 was used.

(2) Expansion of CTLs Maintaining Specific Activity by Anti-CD3 Antibody

CTLs prepared in item (1) of Example 8 were washed with 5HRPMI, and then made into a suspension having a concentration of $5 \times 10^4$ cells/ml. On the other hand, allogenic PBMCs not having HLA-A24 and HLA-A2.1 which were collected in the same manner as in item (1) of Example 1-1 were subjected to X-ray irradiation (3300R), and the cells were washed with the medium and then made into a suspen-

TABLE 11

| Sample | Addition of Sample* | | Expansion Fold (Times) | Peptide Pulse¶ | Target Cells | Cytotoxic Activity (%) E/T Ratio | | |
|---|---|---|---|---|---|---|---|---|
| | During CTL Induction | During Expansion | | | | 2 | 7 | 20 |
| Control | − | − | 287 | − | 221A2.1 | 0 | 3.8 | 4.1 |
| | − | − | 287 | + | 221A2.1 | 8.1 | 27.5 | 43.5 |
| | − | − | 287 | − | 888mel | 32.5 | 44.8 | 43.7 |
| | − | − | 287 | − | 624mel | 27.4 | 55.8 | 81.6 |
| | | | | | | E/T Ratio | | |
| | | | | | | 2 | 6 | 17 |
| Hyaluronic Acid | + | + | 217 | − | 221A2.1 | 0 | 0 | 0 |
| | + | + | 217 | + | 221A2.1 | 9.1 | 52.8 | 74.4 |
| | + | + | 217 | − | 888mel | 0 | 0 | 0 |
| | + | + | 217 | − | 624mel | 29.6 | 73.8 | 90.6 |

*+: sample being pulsed; −: sample not being pulsed.
¶+: peptide being pulsed; −: peptide not being pulsed.

As a result, in the group with addition of hyaluronic acid during the CTL induction and during the expansion, the CTLs maintained a specific, high cytotoxic activity even after the expansion for 14 days. On the other hand, in the group without addition of the sample during the CTL induction and during the expansion, its activity was clearly lowered. In addition, with regard to the specific cytotoxic activity for the tumor cell line, in the group with addition of hyaluronic acid during the CTL induction and during the expansion, the CTLs maintained a specific, high cytotoxic activity even after the expansion for 14 days. In other words, it was clarified that the expansion of CTLs can be also carried out in a state in which a specific, high cytotoxic activity was maintained for a long period of time during the expansion of anti-tumor-associated antigen(MART1)-CTLs by adding hyaluronic acid during the CTL induction and during the expansion.

sion having a concentration of $5 \times 10^6$ cells/ml. These CTLs in an amount of $3.0 \times 10^4$ cells and allogenic PBMCs in an amount of 4 to $10 \times 10^6$ cells were suspended in 10 ml of 5HRPMI, and anti-CD3 antibody (manufactured by Janssen-Kyowa) was further added thereto so as to have a final concentration of 50 ng/ml. The mixture was placed into a flask of 12.5 cm² (manufactured by Falcon), and the cells were cultured in a wet-type $CO_2$ incubator at 37° C. for 14 days. During the culture, there were set a group with addition of hyaluronic acid as a sample (a final concentration: 10 μg/ml) and a group without addition of the sample. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. During this culture, hyaluronic acid was added to the medium for the group with addition of the sample so as to have a final concentration of 10 µg/ml. On the fourteenth day after the initiation of the expansion, the specific cytotoxic activity of CTLs was determined in the same manner as in item (3) of Example 1-1. The determination results are shown in Table 12.

On the other hand, the expansion according to the REM method was carried out as follows. Allogenic PBMCs not having HLA-A24 and HLA-A2.1 were subjected to X-ray irradiation (3300R), and the cells were washed with the medium and then made into a suspension having a concentration of $5 \times 10^6$ cells/ml. In addition, EBV-B cells were subjected to X-ray irradiation (8000R), and the cells were washed with the medium and then made into a suspension having a concentration of $1 \times 10^6$ cells/ml. The CTLs prepared in item (1) of Example 8-1 in an amount of $3.0 \times 10^4$ cells and the allogenic PBMCs in an amount of 4 to $10 \times 10^6$ cells, and the EBV-B cells in an amount of $2.5 \times 10^6$ cells were suspended in 10 ml of 5HRMPI, and anti-CD3 antibody (manufactured by Janssen-Kyowa) was further added so as to have a final concentration of 50 ng/ml. The mixture was placed into a flask of 12.5 cm² (manufactured by Falcon), and the cells were cultured in a wet-type $CO_2$ incubator at 37° C. for 14 days. During the culture, there were set a group with addition of hyaluronic acid as a sample so as to have a final concentration of 10 µg/ml and a group without addition of the sample. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. During this culture, hyaluronic acid was added to the medium for the group with addition of the sample so as to have a final concentration of 10 µg/ml. On the fourteenth day after the initiation of the expansion, the specific cytotoxic activity of CTLs was determined in the same manner as in item (3) of Example 1-1. The determination results are shown in Table 12.

On the other hand, when hyaluronic acid was added during the CTL induction and during the expansion, the cytotoxic activity of CTLs could be maintained at a sufficiently high level after the expansion for 14 days even in a case where the EBV-B cells were not added. Furthermore, the antigen-specific cytotoxic activity of CTLs after the expansion according to the present invention was higher as compared to that of the cells obtained according to the REM method.

In addition, when the expansion was carried out according to the REM method, the cytotoxic activity could be maintained at a higher level as compared to that of the CTLs obtained by expanding the CTL cells which had been induced by a conventional technique simply by the REM method, if hyaluronic acid, one of the substances having effects for maintaining CTL activity in the method of the present invention, was added at the stage of CTL induction prior to the expansion.

In other words, in the method for expansion of CTLs according to the present invention, the EBV-B cells which are essential in the REM method are not required, so that the risks involved in the use of the EBV-B cells can be avoided. Furthermore, there can be maintained the activity of CTLs higher than that obtained by the REM method. From these findings, the method for expanding CTL cells of the present invention is a method which is safer and more excellent than the REM method.

Furthermore, when hyaluronic acid is introduced into the REM method, an even higher activity can be maintained. Therefore, hyaluronic acid can be applied to all sorts of methods for expanding CTLs. In other words, the CTLs can be expanded in a state in which a specific, high cytotoxic activity is maintained for a long period of time by utilizing the substance usable in the present invention in various methods for expanding CTLs.

EXAMPLE 9

Preparation of Fibronectin Fragment (1) Preparation of Fibronectin Fragment

H-271, a fragment derived from human fibronectin, was prepared from *Escherichia coli* HB101/pHD101 (FERM BP-2264) in accordance with the method described in U.S. Pat. No. 5,198,423.

TABLE 12

| Sample | Addition of Sample* | | | Expansion Fold (Times) | Peptide Pulse¶ | Cytotoxic Activity (%) E/T Ratio 10 |
|---|---|---|---|---|---|---|
| | During CTL Induction | During Expansion | Addition of EBV-B Cells† | | | |
| Control | − | − | − | 392 | − | 6.2 |
| | − | − | − | 392 | + | 10.6 |
| Hyaluronic Acid | + | + | − | 335 | − | 2.3 |
| | + | + | − | 335 | + | 60.0 |
| REM Method | − | − | + | 427 | − | 11.5 |
| | − | − | + | 427 | + | 52.8 |
| REM Method + Hyaluronic Acid | + | + | + | 587 | − | 8.1 |
| | + | + | + | 587 | + | 95.5 |

*+: sample being pulsed; −: sample not being pulsed.
†+: EMV-B cells being pulsed; −: EMV-B cells not being pulsed.
¶+: peptide being pulsed; −: peptide not being pulsed.

As a result, the CTLs which were induced without addition of hyaluronic acid (without addition of CTL activity maintaining substance) maintained a high cytotoxic activity when the expansion was carried out according to the REM method. However, the cytotoxic activity was drastically lowered when the expansion was carried out by a method without using the EBV-B cells.

In addition, H-296, CH-271 and CH-296, fragments derived from human fibronectin, were each prepared from a culture obtained by culturing *Escherichia coli* HB101/pHD102 (FERM P-10721), *Escherichia coli* HB101/pCH101 (FERM BP-2799) or *Escherichia coli* HB101/pCH102 (FERM BP-2800), in accordance with the method described in the above-mentioned gazette.

C-274, a fragment derived from human fibronectin, was prepared from a culture obtained by culturing *Escherichia coli* JM109/pTF7221 (FERM BP-1915) in accordance with the method described in U.S. Pat. No. 5,102,988.

C-CS1, a fragment derived from human fibronectin, was prepared from a culture obtained by culturing *Escherichia coli* HB101/pCS25 (FERM BP-5723) in accordance with the method described in Japanese Patent Gazette No.3104178.

CHV-89 and CHV-179, fragments derived from human fibronectin, were each prepared from a culture obtained by culturing *Escherichia coli* HB101/pCHV89 (FERM P-12182) or *Escherichia coli* HB101/pCHV179 (FERM P-12183), in accordance with the method described in Japanese Patent Gazette No. 2729712.

In addition, CHV-90, a fragment derived from human fibronectin, was prepared in accordance with the method described in the above-mentioned gazette. Concretely, a plasmid pCHV90 was constructed in accordance with the procedures described in the gazette, and thereafter a transformant carrying the plasmid was cultured, and CHV-90 was prepared from the culture.

CHV-181, a fragment derived from human fibronectin, was prepared by constructing the plasmid (pCHV181) comprising a DNA encoding CHV-181 in accordance with the method described in WO 97/18318, thereafter culturing *Escherichia coli* HB101/pCHV181 into which the plasmid had been introduced, and preparing the fragment from the culture in the same manner as that for the above CHV-179.

(2) Preparation of CHV-92

As to pCHV181, a plasmid for expressing the above-mentioned polypeptide CHV-181, there was constructed a plasmid CHV92 having deletion of a region encoding a III-13 region in the region encoding CHV-181. The deletion procedures were performed in accordance with procedures for deleting a III-14 coding region from a plasmid pCHV179, which are described in Japanese Patent Gazette No. 2729712.

*Escherichia coli* HB101 (*Escherichia coli* HB101/pCHV92) transformed with the above-mentioned plasmid pCHV92 was cultured, and the purification procedures were carried out in accordance with the method of purifying the CHV-89 polypeptide described in Japanese Patent Gazette No. 2729712, to obtain a purified CHV-92 preparation from the resulting culture.

(3) Preparation of H-275-Cys

A plasmid for expressing a polypeptide H-275-Cys was constructed in accordance with the following procedures. Concretely, a plasmid pCH102 was prepared from *Escherichia coli* HB101/pCH102 (FERM BP-2800). PCR was carried out using a primer 12S having the nucleotide sequence shown in SEQ ID NO: 14 of Sequence Listing and a primer 14A having the nucleotide sequence shown in SEQ ID NO: 15 of Sequence Listing with this plasmid as a template, to give a DNA fragment of about 0.8 kb, encoding a heparin binding polypeptide of fibronectin. The resulting DNA fragment was digested with NcoI and BamHI (both manufactured by Takara Shuzo Co., Ltd.), and thereafter ligated with pTV118N (manufactured by Takara Shuzo Co., Ltd.) digested with NcoI and BamHI, to construct a plasmid pRH1.

A plasmid vector pINIII-ompA$_1$ [Ghrayeb J. et al., *EMBO J.*, 3(10), 2437-2442 (1984)] was digested with BamHI and HincII (manufactured by Takara Shuzo Co., Ltd.) to collect a DNA fragment of about 0.9 kb, containing a lipoprotein terminator region. This fragment was mixed and ligated with the above-mentioned plasmid pRH1 which had been digested with BamHI and HincII, to give a plasmid pRH1-T containing a lac promoter, a DNA fragment encoding a heparin binding polypeptide and a lipoprotein terminator in this order.

The reaction for PCR was carried out by using a primer Cys-A having the nucleotide sequence shown in SEQ ID NO: 16 of Sequence Listing and a primer Cys-S having the nucleotide sequence shown in SEQ ID NO: 17 of Sequence Listing with this plasmid pRH1-T as a template. Thereafter, the collected amplified DNA fragment was digested with NotI (manufactured by Takara Shuzo Co., Ltd.), and the DNA fragment was further self-ligated. A cyclic DNA thus obtained was digested with SpeI and ScaI (manufactured by Takara Shuzo Co., Ltd.) to give a DNA fragment of 2.3 kb, and the resulting fragment was mixed and ligated with a DNA fragment of 2.5 kb, obtained by digesting the plasmid pRH1-T with SpeI and ScaI (manufactured by Takara Shuzo Co., Ltd.), to give a plasmid pRH-Cys. The plasmid encodes a polypeptide (H-275-Cys) in which four amino acids Met-Ala-Ala-Ser were added to an N-terminal side of the above-mentioned H-271, and further Cys was added to a C-terminal of the H-271.

The polypeptide H-275-Cys was prepared by the following method. *Escherichia coli* HB101 transformed with the above-mentioned plasmid pRH-Cys (*Escherichia coli* HB101/pRH-Cys) was cultured overnight at 37° C. in 120 ml of an LB medium. The cells collected from the culture medium were suspended in 40 ml of a buffer for disruption (50 mM Tris-HCl, 1 mM EDTA, 150 mM NaCl, 1 mM DTT, 1 mM PMSF, pH 7.5), and the suspension was subjected to ultrasonic treatment to disrupt the cells. The supernatant obtained by centrifugation was subjected to HiTrap-heparin column (manufactured by Pharmacia) which had been equilibrated with a purifying buffer (50 mM Tris-HCl, pH 7.5). The non-adsorbed fraction in the column was washed with the same buffer, and thereafter the elution was carried out with a purifying buffer having a 0 to 1 M NaCl concentration gradient. The eluate was analyzed by SDS-PAGE, and fractions corresponding to a molecular weight of H-275-Cys were collected to give a purified H-275-Cys preparation.

EXAMPLE 10

Expansion of CTLs Maintaining Specific Cytotoxic Activity Using Fibronectin Fragment (FNfr)

(1) Induction of Anti-Influenza Virus Memory CTLs

The induction of anti-influenza virus memory CTLs was performed in accordance with the method described in item (2) of Example 1-1 using the PBMCs isolated and stored in accordance with the method described in item (1) of Example 1-1. During the induction, each of the fibronectin fragments (hereinafter referred to as FNfr) described in Example 9 was added so as to have a final concentration of 10 μg/ml. As a control, a group without addition of FNfr was also set.

The cytotoxic activity of CTLs which were thus prepared on the fourteenth day after the initiation of induction was evaluated in the same manner as in item (3) of Example 1-1. As a result, the specific cytotoxic activity was induced immediately after the induction, but there were hardly any differences in the cytotoxic activity by the presence or absence of addition of FNfr during the induction.

(2) Expansion of CTLs

CTLs prepared in item (1) of Example 10 were expanded in the same manner as in item (4) of Example 1-1. During the expansion, FNfr, which had been added during the CTL induction, was added so as to have a final concentration of 10 μg/ml. FNfr was not added to the control group in which the induction was carried out without addition of FNfr. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant an, thereafter adding to each flask 5 ml of 5HRPMI containing 60 U/ml of IL-2 or RPMI 1640 medium (manufactured by Bio Whittaker) containing 10% Hyclone FBS, 0.1 mM nonessential amino acids, 1 mM sodium pyruvate, 2 mM L-glutamine (all manufactured by Bio Whittaker), 10 mM HEPES (manufactured by nakalai tesque) and 1% streptomycin-penicillin (manufactured by Gibco BRL) (hereinafter simply referred to as 10HycloneRPMI) were carried out every 2 to 3 days. During the expansion, FNfr was added so as to have the same concentration as that mentioned above to a medium for the group with addition of FNfr. On the fourteenth day after the initiation of the expansion, the specific cytotoxic activity of CTL was determined in the same manner as in item (3) of Example 1-1. The degree in which the specific cytotoxic activity before the expansion is maintained was calculated as "specific cytotoxic activity maintenance (%)." The "specific cytotoxic activity maintenance (%)" was calculated according to the following equation 2:

Specific Cytotoxic Activity Maintenance (%)={Specific Cytotoxic Activity (%) After Expansion/Specific Cytotoxic Activity (%) Before Expansion}×100    Equation 2

The determination results are shown in Table 13.

TABLE 13

| Medium | Fibronectin Fragment | Expansion Fold (Times) | Cytotoxic Activity Maintenance (%) |
|---|---|---|---|
| | | | E/T Ratio = 3 |
| 5HRPMI | Control (Without Addition of FNfr) | 417 | 17.3 |
| | CH-271 | 397 | 53.5 |
| | H-296 | 413 | 49.3 |
| | C-CS1 | 393 | 49.3 |
| | CHV-92 | 370 | 66.2 |
| 10HycloneRPMI | Control (Without Addition of FNfr) | 130 | 48.1 |
| | CH-271 | 132 | 250.8 |
| | H-296 | 75 | 162.3 |
| | H-271 | 52 | 72.2 |
| | C-CS1 | 130 | 100.2 |
| | CHV-92 | 35 | 157.8 |
| | | | E/T Ratio = 10 |
| 10HycloneRPMI | Control (Without Addition of FNfr) | 42 | 46.3 |
| | CHV-89 | 35 | 69.0 |
| | CHV-90 | 36 | 75.6 |

As shown in Table 13, the CTLs of the group with addition of various fibronectin fragments during the induction and during the expansion maintained a specific, high cytotoxic activity even after the expansion for 14 days as compared to that of the control without addition of fibronectin fragment. In other words, it was clarified that the CTLs could be expanded in a state in which a high cytotoxic activity was maintained for a long period of time by carrying out the induction and the expansion in the co-presence of the fibronectin fragment.

EXAMPLE 11

Induction and Expansion of CTLs in the Presence of Fibronectin (1) Induction of Anti-Influenza Virus Memory CTLs The induction of anti-influenza virus memory CTLs was performed in accordance with the method described in item (2) of Example 1-1 using the PBMCs isolated and stored in accordance with the method described in item (1) of Example 1-1. During the induction, fibronectin (manufactured by Calbiochem) was added in place of FNfr so as to have a final concentration of 10 μg/ml (a control being without addition). The cytotoxic activity of CTLs on the fourteenth day after the initiation of the induction was determined in the same manner as in item (3) of Example 1-1. As a result, there were hardly any differences in the cytotoxic activity by the presence or absence of the addition of FNfr during the induction.

(2) Expansion of CTLs

CTLs prepared in item (1) of Example 11 were expanded in the same manner as in item (2) of Example 10. During the expansion, to the group with addition of fibronectin during the induction, fibronectin (manufactured by Calbiochem) was added, so as to have a final concentration of 10 μg/ml (a control without addition). The cytotoxic activity of the CTLs was determined in the same manner as that of item (3) of Example 1-1, and to which degree the specific cytotoxic activity before the expansion is maintained was calculated as "specific cytotoxic activity maintenance (%)." The "specific cytotoxic activity maintenance (%)" was calculated according to the above equation 2.

The determination results are shown in Table 14.

TABLE 14

| | Expansion Fold (Times) | Cytotoxic Activity Maintenance (%) E/T Ratio = 3 |
|---|---|---|
| Control (Without Addition of FNfr) | 130 | 48.1 |
| Fibronectin | 157 | 148.9 |

As shown in Table 14, the group in which the induction of CTLs and the expansion were carried out in the presence of fibronectin maintained a high cytotoxic activity. On the other hand, the cytotoxic activity of the control without addition of fibronectin during the induction of CTLs and during the expansion was clearly lowered. In other words, it was clarified that CTL could be expanded in a state in which a specific cytotoxic activity was maintained for a long period of time by adding fibronectin during the induction of CTLs and during the expansion.

EXAMPLE 12

Expansion of CTLs in the Presence of Immobilized Fibronectin (FN) Fragment (1) Immobilization of FN Fragment A fibronectin fragment was immobilized to a culture equipment (vessel) used in the following experiment. Concretely, PBS containing various fibronectin fragments (final concentration: 10 μg/ml) was added in an amount of 1 to 2 ml each to a 24-well cell culture plate and a 12.5 $cm^2$ flask. The plate and flask were subjected to incubation at room temperature for 2 hours, and then stored at 4° C. until use. In addition, the plate and the flask were washed twice with PBS before use.

(2) Induction of Anti-Influenza Virus Memory CTL

The induction of anti-influenza virus memory CTLs was performed in accordance with the method described in item (2) of Example 1-1 using the PBMCs isolated and stored in accordance the method described in item (1) of Example 1-1.

During the induction, a plate immobilized with FNfr was used as a culture equipment (for a control, a plate without immobilized treatment was used). The cytotoxic activity of CTLs after the induction was evaluated in the same manner as in item (3) of Example 1-1. As a result, there were hardly any differences in the cytotoxic activity by the presence or absence of immobilization of FNfr to the plate used during the induction.

(3) Expansion of CTLs

The CTLs prepared in item (2) of Example 12 were expanded in the same manner as in item (2) of Example 10. During the expansion, flasks with various FNfr's immobilized thereto were used as culture equipments (for a control, a flask without immobilized treatment was used). In addition, 10Hyclone/RPMI was used as a medium.

To which degree the cytotoxic activity of CTLs thus expanded was maintained as compared to that before the expansion was evaluated as "specific cytotoxic activity maintenance (%)." The "specific cytotoxic activity maintenance (%)" was calculated according to the above-mentioned equation 2.

The determination results are shown in Table 15.

TABLE 15

| Fibronectin Fragment | Expansion Fold (Times) | Cytotoxic Activity Maintenance (%) E/T Ratio = 3 |
| --- | --- | --- |
| Control (Without Immobilization of FNfr) | 130 | 48.1 |
| CH-271 | 128 | 95.4 |
| H-296 | 27 | 95.0 |
| H-271 | 40 | 133.9 |
| C-CS1 | 130 | 73.8 |
| H-275-Cys | 87 | 137.7 |
| CHV-92 | 122 | 92.7 |

As shown in Table 15, in the group in which the culture equipment (plate, flask) immobilized with the fibronectin fragment was used during the induction of CTLs and during the expansion, the CTLs maintained a specific, high cytotoxic activity even after the expansion. On the other hand, in the control in which the equipment without immobilization with the fibronectin fragment was used during the induction of CTLs and during the expansion, the cytotoxic activity was clearly lowered. In other words, it was clarified that the CTLs could be expanded in a state in which a high cytotoxic activity was maintained for a long period of time, comparable to that of the fragment dissolved in the medium, by using the immobilized fibronectin fragment.

EXAMPLE 13

Expansion of CTLs Maintaining Tumor-Associated Antigen-Specific Cytotoxic Activity (1) Induction of Anti-Tumor-Associated Antigen (MART1)-Specific CTLs The induction of anti-tumor-associated antigen (melanoma antigen recognized by T cell, MART1)-specific CTLs was performed in accordance with the method described in item (1) of Example 7-2 using the PBMCs isolated and stored in accordance with the method described in item (1) of Example 1-1. During the induction, an anti-HGF antibody was added so as to have a final concentration of 2 µg/ml. As a control, a group without addition of the sample was also set.

The cytotoxic activity of CTLs which were thus prepared on the thirty-fifth day after the initiation of the induction was evaluated in the same manner as in item (3) of Example 1-1. In the evaluation, as target cells, there were used HLA-A2.1-having EBV-transformed B cells (name of cells: 221A2.1), which were cultured overnight together with an epitope peptide, or in the absence of the epitope peptide, HLA-A2.1-having cancer cell strain (name of cells: 624mel; HLA-A 2.1-having MART1-expressing cell) or HLA-A2.1-not having cancer cell strain (name of cells: 938mel; HLA-A 2.1-not having MART1-expressing cell) which was cultured for two nights in the presence of 100 U/ml of IFN-γ.

As a result, the specific cytotoxic activity was induced immediately after the induction, but there were hardly any differences in the cytotoxic activity by the presence or absence of the addition of the sample during the induction.

(2) Expansion of CTLs

The CTLs prepared in item (1) of Example 13 were expanded in the same manner as in item (4) of Example 1-1. During the expansion, there were set a group with addition of anti-HGF antibody, which had been added during the CTL induction in item (1) of Example 13, so as to have a concentration of 2 µg/ml, and a group without addition of the sample at all from the stage of induction. Stimulation by a peptide was not added at all during the expansion. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 2 µg/ml anti-HGF antibody to each flask were carried out every 2 to 3 days. Here, in the group without addition of the sample, the sample was not added even during the medium exchange. On the fourteenth day after the initiation of the expansion, the specific cytotoxic activity of CTLs was determined in the same manner as in item (3) of Example 1-1. The determination results are shown in Table 16.

TABLE 16

| Sample | Addition of Sample* During CTL Induction | Addition of Sample* During Expansion | Expansion Fold (Times) | Peptide Pulse¶ | Target Cells | Cytotoxic Activity (%) E/T Ratio 3 |
| --- | --- | --- | --- | --- | --- | --- |
| Control | − | − | 83 | − | 221A2.1 | 0 |
|  | − | − | 83 | + | 221A2.1 | 31.7 |
|  | − | − | 83 | − | 938mel | 2.3 |
|  | − | − | 83 | − | 624mel | 60.0 |
| Anti-HGF | + | + | 107 | − | 221A2.1 | 0 |

TABLE 16-continued

| Sample | Addition of Sample* | | Expansion Fold (Times) | Peptide Pulse¶ | Target Cells | Cytotoxic Activity (%) E/T Ratio 3 |
|---|---|---|---|---|---|---|
| | During CTL Induction | During Expansion | | | | |
| Antibody | + | + | 107 | + | 221A2.1 | 59.1 |
| | + | + | 107 | − | 938mel | 0 |
| | + | + | 107 | − | 624mel | 81.2 |

*+: sample being pulsed; −: sample not being pulsed.
¶+: peptide being pulsed; −: peptide not being pulsed.

As a result, in the group with addition of the anti-HGF antibody during the CTL induction and during the expansion, the CTLs maintained a specific, high cytotoxic activity even after the expansion for 14 days. On the other hand, in the group without addition of these samples during the CTL induction and during the expansion, its activity was clearly lowered. In addition, with regard to the specific cytotoxic activity for a tumor cell line, in the group with addition of the anti-HGF antibody during the CTL induction and during the expansion, the CTLs maintained a specific, high cytotoxic activity even after the expansion was carried out for 14 days. In other words, it was clarified that even during the expansion of anti-tumor-associated antigen(MART1)-CTLs, the expansion of CTLs could be carried out in a state in which a specific, high cytotoxic activity was maintained by adding the anti-HGF antibody during the CTL induction and during the expansion.

Sequence Listing Free Text

SEQ ID NO: 1 is an amino acid sequence of a peptide fragment derived from human fibronectin named C-274.
SEQ ID NO: 3 is an amino acid sequence of a peptide fragment derived from human fibronectin named H-271.
SEQ ID NO: 4 is an amino acid sequence of a peptide fragment derived from human fibronectin named H-296.
SEQ ID NO: 5 is an amino acid sequence of a peptide fragment derived from human fibronectin named CH-271.
SEQ ID NO: 6 is an amino acid sequence of a peptide fragment derived from human fibronectin named CH-296.
SEQ ID NO: 7 is an amino acid sequence of a peptide fragment derived from human fibronectin named C-CS1.
SEQ ID NO: 8 is an amino acid sequence of a peptide fragment derived from human fibronectin named CHV-89.
SEQ ID NO: 9 is an amino acid sequence of a peptide fragment derived from human fibronectin named CHV-90.
SEQ ID NO: 10 is an amino acid sequence of a peptide fragment derived from human fibronectin named CHV-92.
SEQ ID NO: 11 is an amino acid sequence of a peptide fragment derived from human fibronectin named CHV-179.
SEQ ID NO: 12 is an amino acid sequence of a peptide fragment derived from human fibronectin named CHV-181.
SEQ ID NO: 13 is an amino acid sequence of a peptide fragment derived from human fibronectin named H-275-Cys.
SEQ ID NO: 14 is a nucleotide sequence of a primer 12S.
SEQ ID NO: 15 is a nucleotide sequence of a primer 14A.
SEQ ID NO: 16 is a nucleotide sequence of a primer Cys-A.
SEQ ID NO: 17 is a nucleotide sequence of primer Cys-S.
SEQ ID NO: 18 is an amino acid sequence of a peptide designed on the basis of an HLA-A2.1-binding peptide derived from a matrix protein of influenza virus.
SEQ ID NO: 19 is an amino acid sequence of a peptide designed on the basis of an HLA-A2.1-binding peptide derived from a melanoma antigen MAGE3.
SEQ ID NO: 20 is an amino acid sequence of a peptide designed on the basis of an HLA-A2.1-binding peptide derived from a melanoma antigen MART1.

INDUSTRIAL APPLICABILITY

According to the present invention, there are provided a method for inducing, a method for maintaining and a method for expanding CTL capable of maintaining and/or expanding CTL with maintaining the antigen-specific cytotoxic activity at a high level.

This method is extremely useful in the field of cell remedy such as adoptive immunotherapy requiring a large amount of CTLs. In addition, since the CTL prepared by this method is prepared by a safe method, the CTL can be a cell medicament having very high safety.

The invention claimed is:

1. A method for maintaining cytotoxic T cell having an antigen-specific cytotoxic activity, characterized in that the method comprises the steps of:

incubating a peripheral blood mononuclear cell with an antigen presenting cell in a medium containing effective ingredients consisting essentially of interleukin-2 and a fragment of fibronectin having a molecular weight of from 10 kDa to 180 kDa or a mixture thereof, wherein the fragment of fibronectin is immobilized to an artificial substrate and comprises at least one domain selected from the group consisting of (a) a VLA-4 binding domain (b) a VLA-5 binding domain and (c) a heparin binding domain, and said incubating step gives said peripheral blood mononuclear cell an ability to recognize a desired antigen and induces differentiation of the peripheral blood mononuclear cell to a cytotoxic T cell; and continuously culturing the cytotoxic T cell obtained by the preceding step in the presence of a fragment of fibronectin having a molecular weight of from 10 kDa to 180 kDa or a mixture thereof, wherein the fragment of fibronectin is immobilized to an artificial substrate and comprises at least one domain selected from the group consisting of:
(a) a VLA-4 binding domain,
(b) a VLA-5 binding domain, and
(c) a heparin binding domain.

2. A method for expanding cytotoxic T cell having an antigen-specific cytotoxic activity, characterized in that the method comprises the steps of:

incubating a peripheral blood mononuclear cell with an antigen presenting cell in a medium containing effective ingredients consisting essentially of interleukin-2 and a fragment of fibronectin having a molecular weight of from 10 kDa to 180 kDa or a mixture thereof, wherein the fragment of fibronectin is immobilized to an artificial substrate and comprises at least one domain selected from the group consisting of (a) a VLA-4 binding domain (b) a VLA-5 binding domain and (c) a heparin binding domain, and said incubating step gives said peripheral blood mononuclear cell an ability to recognize a desired antigen and induces differentiation of the peripheral mononuclear cell to a cytotoxic T cell; and incubating the cytotoxic T cell obtained by the preceding step in the presence of anti-CD3 antibody and a fragment of fibronectin having a molecular weight of from 10 kDa to 180 kDa or a mixture thereof, wherein the fragment of fibronectin is immobilized to an artificial substrate and is a fragment having at least one domain selected from the group consisting of:

(a) a VLA-4 binding domain,
(b) a VLA-5 binding domain, and
(c) a heparin binding domain.

3. The method according to claim 2, wherein the cytotoxic T cell is incubated together with a feeder cell in said step.

4. The method according to claim 3, wherein the feeder cell is a non-virus-infected cell.

5. A method for collecting cytotoxic T cell, comprising the step of selecting a cell population rich in cytotoxic T cell having an antigen-specific cytotoxic activity from a culture containing the cytotoxic T cell obtained by the method of claim 1 or 2; and collecting said cell population.

6. The method according to claim 1, wherein the fragment of fibronectin comprises:
   at least one of the amino acid sequences represented by SEQ ID NOS: 1 to 13.

7. The method according to claim 2, wherein the fragment of fibronectin comprises:
   at least one of the amino acid sequences represented by SEQ ID NOS: 1 to 13.

8. The method according to claim 1, wherein the fragment of fibronectin is immobilized to a culture equipment or microbeads.

9. The method according to claim 2, wherein the fragment of fibronectin is immobilized to a culture equipment or microbeads.

* * * * *